(12) United States Patent
Balczewski et al.

(10) Patent No.: US 11,529,523 B2
(45) Date of Patent: Dec. 20, 2022

(54) HANDHELD BRIDGE DEVICE FOR PROVIDING A COMMUNICATION BRIDGE BETWEEN AN IMPLANTED MEDICAL DEVICE AND A SMARTPHONE

(71) Applicant: CARDIAC PACEMAKERS, INC., St. Paul, MN (US)

(72) Inventors: Ron A. Balczewski, Bloomington, MN (US); William J. Linder, Golden Valley, MN (US); Keith R. Maile, New Brighton, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 455 days.

(21) Appl. No.: 16/239,171

(22) Filed: Jan. 3, 2019

(65) Prior Publication Data

US 2019/0201701 A1   Jul. 4, 2019

Related U.S. Application Data

(60) Provisional application No. 62/613,588, filed on Jan. 4, 2018.

(51) Int. Cl.
*A61N 1/372* (2006.01)
*A61N 1/375* (2006.01)
(Continued)

(52) U.S. Cl.
CPC ........ *A61N 1/37223* (2013.01); *A61B 5/0028* (2013.01); *A61B 5/0031* (2013.01);
(Continued)

(58) Field of Classification Search
CPC ............ A61N 1/37223; A61N 1/37217; A61N 1/3756; A61B 5/0028
See application file for complete search history.

(56) References Cited

U.S. PATENT DOCUMENTS

| 3,835,864 A | 9/1974 | Rasor et al. |
| 3,943,936 A | 3/1976 | Rasor et al. |

(Continued)

FOREIGN PATENT DOCUMENTS

| AU | 2008279789 B2 | 10/2011 |
| AU | 2008329620 B2 | 5/2014 |

(Continued)

OTHER PUBLICATIONS

US 8,886,318 B2, 11/2014, Jacobson et al. (withdrawn)
(Continued)

*Primary Examiner* — William J Levicky
(74) *Attorney, Agent, or Firm* — Seager, Tufte & Wickhem LLP

(57) ABSTRACT

A bridge device includes a housing, a plurality of electrodes exposed outside of the housing such that at least two of the plurality of electrodes can be concurrently placed in contact with a patient's skin. A controller is disposed within the housing. A first communications module is operably coupled to the controller and to the at least two of the plurality of electrodes. The first communications module is configured to allow the controller to communicate with an implantable medical device via at least two of the plurality of electrodes using conducted communication. A second communications module is operably coupled to the controller and is configured to allow the controller to communicate with a remote device external to the patient.

14 Claims, 12 Drawing Sheets

(51) Int. Cl.

| | | |
|---|---|---|
| H04W 4/80 | (2018.01) | |
| A61N 1/365 | (2006.01) | |
| A61B 5/07 | (2006.01) | |
| A61B 5/00 | (2006.01) | |
| H04M 1/72409 | (2021.01) | |
| H04W 84/18 | (2009.01) | |
| A61N 1/362 | (2006.01) | |
| A61N 1/39 | (2006.01) | |
| A61B 5/318 | (2021.01) | |

(52) U.S. Cl.
CPC .............. *A61B 5/076* (2013.01); *A61B 5/686* (2013.01); *A61N 1/36514* (2013.01); *A61N 1/36521* (2013.01); *A61N 1/375* (2013.01); *A61N 1/3756* (2013.01); *A61N 1/37205* (2013.01); *A61N 1/37217* (2013.01); *A61N 1/37247* (2013.01); *H04M 1/72409* (2021.01); *H04W 4/80* (2018.02); *A61B 5/318* (2021.01); *A61N 1/3627* (2013.01); *A61N 1/3727* (2013.01); *A61N 1/37235* (2013.01); *A61N 1/3956* (2013.01); *A61N 1/3968* (2013.01); *H04W 84/18* (2013.01)

(56) References Cited

U.S. PATENT DOCUMENTS

| | | | |
|---|---|---|---|
| 4,142,530 A | 3/1979 | Wittkampf | |
| 4,151,513 A | 4/1979 | Menken et al. | |
| 4,157,720 A | 6/1979 | Greatbatch | |
| RE30,366 E | 8/1980 | Rasor et al. | |
| 4,243,045 A | 1/1981 | Maas | |
| 4,250,884 A | 2/1981 | Hartlaub et al. | |
| 4,256,115 A | 3/1981 | Bilitch | |
| 4,263,919 A | 4/1981 | Levin | |
| 4,310,000 A | 1/1982 | Lindemans | |
| 4,312,354 A | 1/1982 | Walters | |
| 4,323,081 A | 4/1982 | Wiebusch | |
| 4,357,946 A | 11/1982 | Dutcher et al. | |
| 4,365,639 A | 12/1982 | Goldreyer | |
| 4,440,173 A | 4/1984 | Hudziak et al. | |
| 4,476,868 A | 10/1984 | Thompson | |
| 4,522,208 A | 6/1985 | Buffet | |
| 4,537,200 A | 8/1985 | Widrow | |
| 4,556,063 A | 12/1985 | Thompson et al. | |
| 4,562,841 A | 1/1986 | Brockway et al. | |
| 4,593,702 A | 6/1986 | Kepski et al. | |
| 4,593,955 A | 6/1986 | Leiber | |
| 4,630,611 A | 12/1986 | King | |
| 4,635,639 A | 1/1987 | Hakala et al. | |
| 4,674,508 A | 6/1987 | DeCote | |
| 4,712,554 A | 12/1987 | Garson | |
| 4,729,376 A | 3/1988 | DeCote | |
| 4,754,753 A | 7/1988 | King | |
| 4,759,366 A | 7/1988 | Callaghan | |
| 4,776,338 A | 10/1988 | Lekholm et al. | |
| 4,787,389 A | 11/1988 | Tarjan | |
| 4,793,353 A | 12/1988 | Borkan | |
| 4,819,662 A | 4/1989 | Heil et al. | |
| 4,858,610 A | 8/1989 | Callaghan et al. | |
| 4,886,064 A | 12/1989 | Strandberg | |
| 4,887,609 A | 12/1989 | Cole | |
| 4,928,688 A | 5/1990 | Mower | |
| 4,967,746 A | 11/1990 | Vandegriff | |
| 4,987,897 A | 1/1991 | Funke | |
| 4,989,602 A | 2/1991 | Sholder et al. | |
| 5,012,806 A | 5/1991 | De Bellis | |
| 5,036,849 A | 8/1991 | Hauck et al. | |
| 5,040,534 A | 8/1991 | Mann et al. | |
| 5,058,581 A | 10/1991 | Silvian | |
| 5,078,134 A | 1/1992 | Heilman et al. | |
| 5,109,845 A | 5/1992 | Yuuchi et al. | |
| 5,113,859 A | 5/1992 | Funke | |
| 5,113,869 A | 5/1992 | Nappholz et al. | |
| 5,117,824 A | 6/1992 | Keimel et al. | |
| 5,127,401 A | 7/1992 | Grevious et al. | |
| 5,133,353 A | 7/1992 | Hauser | |
| 5,144,950 A | 9/1992 | Stoop et al. | |
| 5,170,784 A | 12/1992 | Ramon et al. | |
| 5,179,945 A | 1/1993 | Van Hofwegen et al. | |
| 5,193,539 A | 3/1993 | Schulman et al. | |
| 5,193,540 A | 3/1993 | Schulman et al. | |
| 5,241,961 A | 9/1993 | Henry | |
| 5,243,977 A | 9/1993 | Trabucco et al. | |
| 5,259,387 A | 11/1993 | DePinto | |
| 5,269,326 A | 12/1993 | Verrier | |
| 5,284,136 A | 2/1994 | Hauck et al. | |
| 5,300,107 A | 4/1994 | Stokes et al. | |
| 5,301,677 A | 4/1994 | Hsung | |
| 5,305,760 A | 4/1994 | McKown et al. | |
| 5,312,439 A | 5/1994 | Loeb | |
| 5,313,953 A | 5/1994 | Yomtov et al. | |
| 5,314,459 A | 5/1994 | Swanson et al. | |
| 5,318,597 A | 6/1994 | Hauck et al. | |
| 5,324,316 A | 6/1994 | Schulman et al. | |
| 5,331,966 A | 7/1994 | Bennett et al. | |
| 5,334,222 A | 8/1994 | Salo et al. | |
| 5,342,408 A | 8/1994 | deCoriolis et al. | |
| 5,370,667 A | 12/1994 | Alt | |
| 5,372,606 A | 12/1994 | Lang et al. | |
| 5,376,106 A | 12/1994 | Stahmann et al. | |
| 5,383,915 A | 1/1995 | Adams | |
| 5,388,578 A | 2/1995 | Yomtov et al. | |
| 5,404,877 A | 4/1995 | Nolan et al. | |
| 5,405,367 A | 4/1995 | Schulman et al. | |
| 5,411,031 A | 5/1995 | Yomtov | |
| 5,411,525 A | 5/1995 | Swanson et al. | |
| 5,411,535 A | 5/1995 | Fujii et al. | |
| 5,456,691 A | 10/1995 | Snell | |
| 5,458,622 A | 10/1995 | Alt | |
| 5,466,246 A | 11/1995 | Silvian | |
| 5,468,254 A | 11/1995 | Hahn et al. | |
| 5,472,453 A | 12/1995 | Alt | |
| 5,522,866 A | 6/1996 | Fernald | |
| 5,540,727 A | 7/1996 | Tockman et al. | |
| 5,545,186 A | 8/1996 | Olson et al. | |
| 5,545,202 A | 8/1996 | Dahl et al. | |
| 5,571,146 A | 11/1996 | Jones et al. | |
| 5,591,214 A | 1/1997 | Lu | |
| 5,620,466 A | 4/1997 | Haefner et al. | |
| 5,634,938 A | 6/1997 | Swanson et al. | |
| 5,649,968 A | 7/1997 | Alt et al. | |
| 5,662,688 A | 9/1997 | Haefner et al. | |
| 5,674,259 A | 10/1997 | Gray | |
| 5,683,426 A | 11/1997 | Greenhut et al. | |
| 5,683,432 A | 11/1997 | Goedeke et al. | |
| 5,706,823 A | 1/1998 | Wodlinger | |
| 5,709,215 A | 1/1998 | Perttu et al. | |
| 5,720,770 A | 2/1998 | Nappholz et al. | |
| 5,728,154 A | 3/1998 | Crossett et al. | |
| 5,741,314 A | 4/1998 | Daly et al. | |
| 5,741,315 A | 4/1998 | Lee et al. | |
| 5,752,976 A | 5/1998 | Duffin et al. | |
| 5,752,977 A | 5/1998 | Grevious et al. | |
| 5,755,736 A | 5/1998 | Gillberg et al. | |
| 5,759,199 A | 6/1998 | Snell et al. | |
| 5,774,501 A | 6/1998 | Halpern et al. | |
| 5,792,195 A | 8/1998 | Carlson et al. | |
| 5,792,202 A | 8/1998 | Rueter | |
| 5,792,203 A | 8/1998 | Schroeppel | |
| 5,792,205 A | 8/1998 | Alt et al. | |
| 5,792,208 A | 8/1998 | Gray | |
| 5,814,089 A | 9/1998 | Stokes et al. | |
| 5,827,216 A | 10/1998 | Igo et al. | |
| 5,836,985 A | 11/1998 | Rostami et al. | |
| 5,836,987 A | 11/1998 | Baumann et al. | |
| 5,842,977 A | 12/1998 | Lesho et al. | |
| 5,855,593 A | 1/1999 | Olson et al. | |
| 5,873,894 A | 2/1999 | Vandegriff et al. | |
| 5,891,184 A | 4/1999 | Lee et al. | |
| 5,897,586 A | 4/1999 | Molina | |
| 5,899,876 A | 5/1999 | Flower | |
| 5,899,928 A | 5/1999 | Sholder et al. | |

(56) References Cited

U.S. PATENT DOCUMENTS

| | | |
|---|---|---|
| 5,919,214 A | 7/1999 | Ciciarelli et al. |
| 5,935,078 A | 8/1999 | Feierbach |
| 5,941,906 A | 8/1999 | Barreras, Sr. et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | DePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,936,007 B2 | 8/2005 | Quy |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |

(56) References Cited

U.S. PATENT DOCUMENTS

| | | |
|---|---|---|
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,313,529 B2 | 12/2007 | Thompson |
| 7,319,905 B1 | 1/2008 | Morgan et al. |
| 7,321,798 B2 | 1/2008 | Muhlenberg et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |

(56) References Cited

U.S. PATENT DOCUMENTS

| | | |
|---|---|---|
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,079 B2 | 10/2011 | Bange |
| 8,046,080 B2 | 10/2011 | Von Arx et al. |
| 8,050,297 B2 | 11/2011 | DelMain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,262,578 B1 | 9/2012 | Bharmi et al. |
| 8,265,556 B2 | 9/2012 | Tekin et al. |
| 8,265,748 B2 | 9/2012 | Liu et al. |
| 8,265,757 B2 | 9/2012 | Mass et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,232 B2 | 10/2012 | Albert et al. |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,401,659 B2 | 3/2013 | Von Arx et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,882 B2 | 8/2013 | Albert et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,137 B2 | 4/2014 | Albert |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |

(56) References Cited

U.S. PATENT DOCUMENTS

| | | | |
|---|---|---|---|
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,026,202 B2 | 5/2015 | Albert |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,220,430 B2 | 12/2015 | Albert |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,247,911 B2 | 2/2016 | Galloway et al. |
| 9,248,300 B2 | 2/2016 | Rys et al. |
| 9,254,092 B2 | 2/2016 | Albert et al. |
| 9,254,095 B2 | 2/2016 | Galloway et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,108 B2 | 4/2016 | Khalil et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,420,956 B2 | 8/2016 | Gopalakrishnan et al. |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,433,796 B2 | 9/2016 | Tahmasian |
| 9,457,193 B2 | 10/2016 | Klimovitch et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishler et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,162 B2 | 1/2017 | Ter-Petrosyan et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,579,062 B2 | 2/2017 | Albert |
| 9,636,511 B2 | 5/2017 | Carney et al. |
| 9,649,042 B2 | 5/2017 | Albert et al. |
| 9,669,223 B2 | 6/2017 | Auricchio et al. |
| 9,687,654 B2 | 6/2017 | Sheldon et al. |
| 9,687,655 B2 | 6/2017 | Pertijs et al. |
| 9,687,659 B2 | 6/2017 | Von Arx et al. |
| 9,694,186 B2 | 7/2017 | Carney et al. |
| 9,707,402 B2 | 7/2017 | Aghassian |
| 9,782,594 B2 | 10/2017 | Stahmann et al. |
| 9,782,601 B2 | 10/2017 | Ludwig |
| 9,789,317 B2 | 10/2017 | Greenhut et al. |
| 9,789,319 B2 | 10/2017 | Sambelashvili |
| 9,808,617 B2 | 11/2017 | Ostroff et al. |
| 9,808,628 B2 | 11/2017 | Sheldon et al. |
| 9,808,631 B2 | 11/2017 | Maile et al. |
| 9,808,632 B2 | 11/2017 | Reinke et al. |
| 9,808,633 B2 | 11/2017 | Bonner et al. |
| 9,808,637 B2 | 11/2017 | Sharma et al. |
| 9,855,414 B2 | 1/2018 | Marshall et al. |
| 9,855,430 B2 | 1/2018 | Ghosh et al. |
| 9,855,435 B2 | 1/2018 | Sahabi et al. |
| 9,861,815 B2 | 1/2018 | Tran et al. |
| 10,080,887 B2 | 9/2018 | Schmidt et al. |
| 10,080,888 B2 | 9/2018 | Kelly et al. |
| 10,080,900 B2 | 9/2018 | Ghosh et al. |
| 10,080,903 B2 | 9/2018 | Willis et al. |
| 10,086,206 B2 | 10/2018 | Sambelashvili |
| 10,118,026 B2 | 11/2018 | Grubac et al. |
| 10,124,163 B2 | 11/2018 | Ollivier et al. |
| 10,124,175 B2 | 11/2018 | Berthiaume et al. |
| 10,130,821 B2 | 11/2018 | Grubac et al. |
| 10,137,305 B2 | 11/2018 | Kane et al. |
| 10,143,847 B1 * | 12/2018 | Edmonson ........... A61B 5/0028 |
| 10,201,710 B2 | 2/2019 | Jackson et al. |
| 10,207,115 B2 | 2/2019 | Echt et al. |
| 10,207,116 B2 | 2/2019 | Sheldon et al. |
| 10,226,197 B2 | 3/2019 | Reinke et al. |
| 10,226,639 B2 | 3/2019 | Zhang |
| 10,232,182 B2 | 3/2019 | Hareland et al. |
| 10,265,503 B2 | 4/2019 | Schmidt et al. |
| 10,265,534 B2 | 4/2019 | Greenhut et al. |
| 10,271,752 B2 | 4/2019 | Regnier et al. |
| 10,278,601 B2 | 5/2019 | Greenhut et al. |
| 10,279,165 B2 | 5/2019 | Seifert et al. |

(56) References Cited

U.S. PATENT DOCUMENTS

| | | |
|---|---|---|
| 10,286,221 B2 | 5/2019 | Sawchuk |
| 10,307,598 B2 | 6/2019 | Ciciarelli et al. |
| 10,328,274 B2 | 6/2019 | Zhang et al. |
| 10,342,981 B2 | 7/2019 | Ghosh et al. |
| 2002/0013613 A1 | 1/2002 | Haller et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Edinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0136418 A1 | 7/2003 | Behm |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0230283 A1 | 11/2004 | Prinzen et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Von Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0294229 A1 | 11/2008 | Friedman et al. |
| 2008/0306359 A1 | 12/2008 | Zdeblick et al. |
| 2009/0018599 A1 | 1/2009 | Hastings et al. |

(56) References Cited

U.S. PATENT DOCUMENTS

| | | |
|---|---|---|
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | M. |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0069983 A1 | 3/2010 | Peacock, III et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0298841 A1 | 11/2010 | Prinzen et al. |
| 2010/0312309 A1 | 12/2010 | Harding |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0270341 A1 | 11/2011 | Ruben et al. |
| 2011/0276102 A1 | 11/2011 | Cohen |
| 2011/0282423 A1 | 11/2011 | Jacobson |
| 2011/0301435 A1 | 12/2011 | Albert et al. |
| 2011/0301439 A1 | 12/2011 | Albert et al. |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0100887 A1 | 4/2012 | Tekin et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172689 A1 | 7/2012 | Albert et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1* | 8/2012 | Tahmasian .......... A61N 1/37217 607/59 |
| 2012/0232565 A1 | 9/2012 | Kveen et al. |
| 2012/0245665 A1 | 9/2012 | Friedman et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0289776 A1 | 11/2012 | Keast et al. |
| 2012/0289815 A1 | 11/2012 | Keast et al. |
| 2012/0290021 A1 | 11/2012 | Saurkar et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1* | 4/2013 | Polefko .......... A61N 1/3605 607/59 |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |

(56) References Cited

U.S. PATENT DOCUMENTS

| | | |
|---|---|---|
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0192611 A1 | 8/2013 | Taepke, II et al. |
| 2013/0196703 A1 | 8/2013 | Masoud et al. |
| 2013/0197320 A1 | 8/2013 | Albert et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0241745 A1 | 9/2013 | Colvin, Jr. et al. |
| 2013/0253309 A1 | 9/2013 | Allan et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0331663 A1 | 12/2013 | Albert et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0050321 A1 | 2/2014 | Albert et al. |
| 2014/0058240 A1 | 2/2014 | Mothilal et al. |
| 2014/0058494 A1 | 2/2014 | Ostroff et al. |
| 2014/0066798 A1 | 3/2014 | Albert |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100624 A1 | 4/2014 | Ellingson |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128758 A1 | 5/2014 | Galloway et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0194760 A1 | 7/2014 | Albert |
| 2014/0206976 A1* | 7/2014 | Thompson ........... A61B 5/0024 600/391 |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0221859 A1 | 8/2014 | Albert |
| 2014/0222015 A1 | 8/2014 | Keast et al. |
| 2014/0222098 A1 | 8/2014 | Baru et al. |
| 2014/0222109 A1 | 8/2014 | Moulder |
| 2014/0228665 A1 | 8/2014 | Albert |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0275928 A1 | 9/2014 | Acquista et al. |
| 2014/0276162 A1 | 9/2014 | Albert et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0343348 A1 | 11/2014 | Kaplan et al. |
| 2014/0371817 A1 | 12/2014 | Mashiach et al. |
| 2014/0371818 A1 | 12/2014 | Bond et al. |
| 2014/0379041 A1 | 12/2014 | Foster |
| 2015/0018660 A1 | 1/2015 | Thomson et al. |
| 2015/0018702 A1 | 1/2015 | Galloway et al. |
| 2015/0025612 A1 | 1/2015 | Haasl et al. |
| 2015/0039041 A1 | 2/2015 | Smith et al. |
| 2015/0045868 A1 | 2/2015 | Bonner et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0073285 A1 | 3/2015 | Albert et al. |
| 2015/0087952 A1 | 3/2015 | Albert et al. |
| 2015/0088155 A1 | 3/2015 | Stahmann et al. |
| 2015/0105836 A1 | 4/2015 | Bonner et al. |
| 2015/0126854 A1 | 5/2015 | Keast et al. |
| 2015/0157861 A1 | 6/2015 | Aghassian |
| 2015/0157866 A1 | 6/2015 | Demmer et al. |
| 2015/0164349 A1 | 6/2015 | Gopalakrishnan et al. |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1* | 7/2015 | Stahmann ........... A61N 1/37217 607/32 |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0230699 A1 | 8/2015 | Berul et al. |
| 2015/0238769 A1 | 8/2015 | Demmer et al. |
| 2015/0258345 A1 | 9/2015 | Smith et al. |
| 2015/0265164 A1 | 9/2015 | Gopalakrishnan et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306401 A1 | 10/2015 | Demmer et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0320328 A1 | 11/2015 | Albert |
| 2015/0321016 A1 | 11/2015 | O'Brien et al. |
| 2015/0328459 A1 | 11/2015 | Chin et al. |
| 2015/0335884 A1 | 11/2015 | Khairkhahan et al. |

(56) References Cited

U.S. PATENT DOCUMENTS

| | | |
|---|---|---|
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0235319 A1 | 8/2016 | Albert |
| 2016/0242665 A1 | 8/2016 | Galloway et al. |
| 2016/0242697 A1 | 8/2016 | Albert |
| 2016/0249823 A1 | 9/2016 | Galloway et al. |
| 2016/0271406 A1* | 9/2016 | Maile .................. A61B 5/0024 |
| 2016/0277097 A1 | 9/2016 | Ludwig et al. |
| 2016/0310048 A1 | 10/2016 | Pang et al. |
| 2016/0317825 A1 | 11/2016 | Jacobson |
| 2016/0331247 A1 | 11/2016 | Albert |
| 2016/0331980 A1 | 11/2016 | Strommer et al. |
| 2016/0367823 A1 | 12/2016 | Cowan et al. |
| 2016/0367827 A1 | 12/2016 | Tahmasian |
| 2017/0014629 A1 | 1/2017 | Ghosh et al. |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0095670 A1 | 4/2017 | Ghaffar et al. |
| 2017/0189681 A1 | 7/2017 | Anderson |
| 2017/0215755 A1 | 8/2017 | Albert et al. |
| 2017/0215756 A1 | 8/2017 | Galloway et al. |
| 2017/0238814 A1 | 8/2017 | Gopalakrishnan et al. |
| 2017/0265806 A1 | 9/2017 | Albert |
| 2017/0281261 A1 | 10/2017 | Shuros et al. |
| 2017/0281952 A1 | 10/2017 | Shuros et al. |
| 2017/0281953 A1 | 10/2017 | Min et al. |
| 2017/0281955 A1 | 10/2017 | Maile et al. |
| 2017/0312531 A1 | 11/2017 | Sawchuk |
| 2018/0256902 A1 | 9/2018 | Toy et al. |
| 2018/0256909 A1 | 9/2018 | Smith et al. |
| 2018/0264262 A1 | 9/2018 | Haasl et al. |
| 2018/0264270 A1 | 9/2018 | Koop et al. |
| 2018/0264272 A1 | 9/2018 | Haasl et al. |
| 2018/0264273 A1 | 9/2018 | Haasl et al. |
| 2018/0264274 A1 | 9/2018 | Haasl et al. |
| 2018/0339160 A1 | 11/2018 | Carroll |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1962953 B1 | 4/2011 |
| EP | 1904166 B1 | 6/2011 |
| EP | 2471452 A1 | 7/2012 |
| EP | 2433675 B1 | 1/2013 |
| EP | 2441491 B1 | 1/2013 |
| EP | 2452721 B1 | 11/2013 |
| EP | 2662113 A3 | 11/2013 |
| EP | 1948296 B1 | 1/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 5/2002 |
| WO | 02098282 A2 | 12/2002 |
| WO | 2005000206 A3 | 1/2005 |
| WO | 2005042089 A1 | 5/2005 |
| WO | 2006065394 A1 | 6/2006 |
| WO | 2006086435 A3 | 8/2006 |
| WO | 2006113659 A1 | 10/2006 |
| WO | 2006124833 A3 | 11/2006 |
| WO | 2007073435 A1 | 6/2007 |
| WO | 2007075974 A2 | 7/2007 |
| WO | 2007150003 A3 | 12/2007 |
| WO | 2009006531 A1 | 1/2009 |
| WO | 2012054102 A1 | 4/2012 |
| WO | 2013080038 A2 | 6/2013 |
| WO | 2013098644 A3 | 7/2013 |
| WO | 2013184787 A1 | 12/2013 |
| WO | 2014120769 A1 | 8/2014 |

OTHER PUBLICATIONS

"Instructions for Use System 1, Leadless Cardiac Pacemaker (LCP) and Delivery Catheter," Nanostim Leadless Pacemakers, pp. 1-28, 2013.

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Seyedi et al., "A Survey on Intrabody Communications for Body Area Network Application," IEEE Transactions on Biomedical Engineering, vol. 60(8): 2067-2079, 2013.

Spickler et al., "Totally Self-Contained Intracardiac Pacemaker," Journal of Electrocardiology, vol. 3(3&4): 324-331, 1970.

Wegmüller, "Intra-Body Communication for Biomedical Sensor Networks," Diss. ETH, No. 17323, 1-173, 2007.

Senseonics, "Improving Connectivity Between a Medical Mobile App and an Implantable Sensor", Sagentia.com, 2 pages, Acessed Oct. 18, 2017.

* cited by examiner

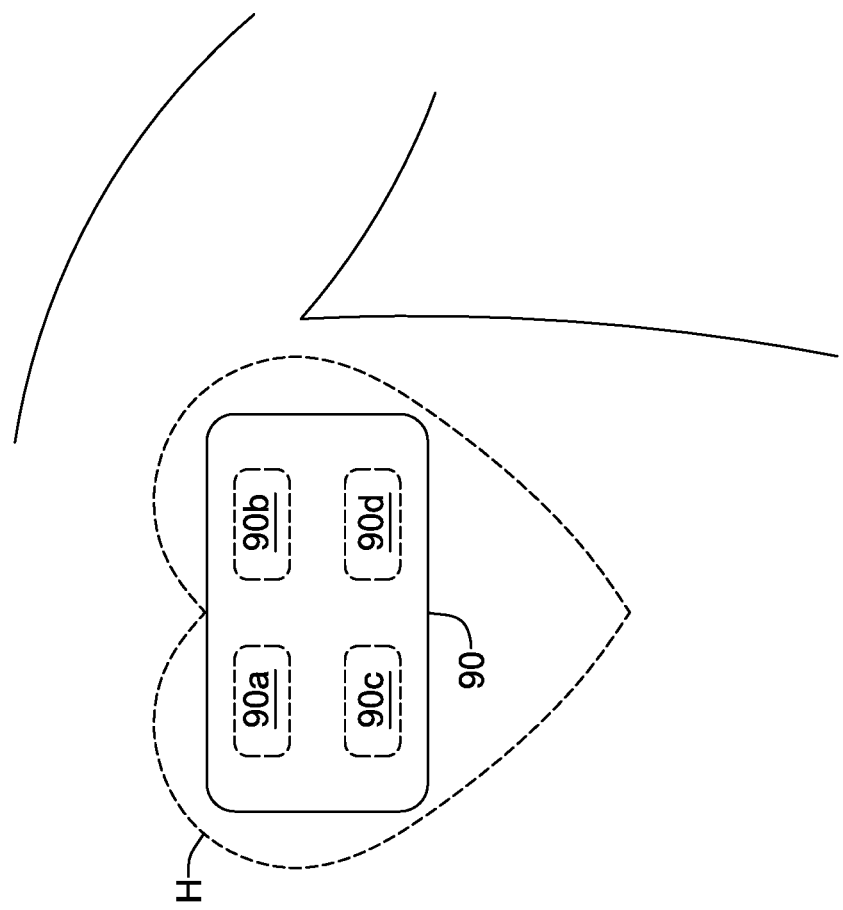
FIG. 9

HANDHELD BRIDGE DEVICE FOR PROVIDING A COMMUNICATION BRIDGE BETWEEN AN IMPLANTED MEDICAL DEVICE AND A SMARTPHONE

CROSS REFERENCE TO RELATED APPLICATIONS

This application claims the benefit of U.S. Provisional Patent Application Ser. No. 62/613,588 filed on Jan. 4, 2018, the disclosure of which is incorporated herein by reference.

TECHNICAL FIELD

The present disclosure pertains to medical devices, and more particularly to medical devices that are configured to communicate with an implanted medical device such as leadless cardiac pacemaker as well as an external device such as a smartphone.

BACKGROUND

Implantable medical devices are commonly used today to monitor physiological or other parameters of a patient and/or deliver therapy to a patient. In one example, to help patients with heart related conditions, various medical devices (e.g., pacemakers, defibrillators, sensors, etc.) can be implanted in a patient's body. Such devices may monitor and in some cases provide electrical stimulation (e.g. pacing, defibrillation, etc.) to the heart to help the heart operate in a more normal, efficient and/or safe manner. In some cases, there is a desire to obtain information from and/or provide commands to an implantable medical device.

SUMMARY

The present disclosure pertains to medical devices, and more particularly to medical devices that are configured to communicate with an implanted medical device such as leadless cardiac pacemaker as well as an external device such as a smartphone. In some cases, the present disclose provides a handheld bridge device for providing a communication bridge between the implanted medical device and the device that is external to the patient.

In a particular example of the disclosure, a handheld bridge device provides a communication bridge between a leadless cardiac pacemaker and a smartphone. The illustrative bridge device includes a housing and a plurality of electrodes that are exposed outside of the housing such that at least two of the plurality of electrodes can be concurrently placed in contact with a patient's skin. A power source is disposed within the housing. A controller is disposed within the housing and is operably powered by the power source. In some cases, the bridge device includes a conducted communications module that is disposed within the housing and is operably coupled to the controller and to the at least two of the plurality of electrodes that can be concurrently placed in contact with a patient's skin. The conducted communications module is configured to allow the controller to communicate with a leadless cardiac pacemaker via at least two of the plurality of electrodes that can be concurrently placed in contact with a patient's skin using conducted communication. The illustrative bridge device may further include a RF communications module that is disposed within the housing and operably coupled to the controller. The RF communications module may be configured to allow the controller to communicate with a smartphone external to the patient using RF communication. In some cases, the bridge device may provide a communication bridge between the leadless cardiac pacemaker and the smartphone such that the leadless cardiac pacemaker can provide information/data to the smartphone and/or the smartphone may provide commands and/or requests to the leadless cardiac pacemaker. It is contemplated that the bridge device may provide one-way or bidirectional communication.

Alternatively or additionally, the bridge device may further include a memory that is operably coupled to the controller such that information received from the leadless cardiac pacemaker by conducted communication via the at least two of the plurality of electrodes can be saved to the memory prior to subsequent communication of the information to the smartphone via the RF communications module.

Alternatively or additionally, the bridge device may further include one or more sensors operatively coupled to the controller for sensing one or more sensed parameters, wherein the controller is configured to communicate the one or more sensed parameters to the smartphone via the RF communications module.

Alternatively or additionally, the one or more sensors may include one or more of an accelerometer, a gyroscope, an impendence sensor, an electrogram sensor, a force sensor, an audio sensor and a button.

Alternatively or additionally, the bridge device may further include a user interface that is operably coupled to the controller. The controller may be configured to communicate with the patient via the user interface and the user interface may include one or more of a vibrator, a speaker and a Light Emitting Diode (LED).

In another example of the disclosure, a bridge device provides a communication bridge between an implantable medical device that is configured to sense cardiac electrical activity of a patient's heart and a remote device that is external to the patient. The bridge device includes a housing and a plurality of electrodes that are exposed outside of the housing such that at least two of the plurality of electrodes can be concurrently placed in contact with a patient's skin. A power source is disposed within the housing, as is a controller that is operably powered at least in part by the power source. The bridge device includes a first communications module that is disposed within the housing and operably coupled to the controller and to the at least two of the plurality of electrodes that can be concurrently placed in contact with a patient's skin, the first communications module being configured to allow the controller to communicate with an implantable medical device via at least two of the plurality of electrodes that can be concurrently placed in contact with a patient's skin using conducted communication. A second communications module is disposed within the housing and is operably coupled to the controller, the second communications module being configured to allow the controller to communicate with a remote device external to the patient.

Alternatively or additionally, the implantable medical device may be a leadless cardiac pacemaker and the remote device may be a smartphone.

Alternatively or additionally, the second communications module may be configured to allow the controller to communicate with the remote device external to the patient using wireless communication.

Alternatively or additionally, the wireless communication may include Radio Frequency (RF) communication.

Alternatively or additionally, the wireless communication may include one or more of bluetooth communication, WiFi communication, inductive communication, infrared (IR) communication and optical communication.

Alternatively or additionally, the second communications module may be configured to allow the controller to communicate with the remote device external to the patient using wired communication.

Alternatively or additionally, the bridge device may further include one or more sensors that are operatively coupled to the controller for sensing one or more sensed parameters, wherein the controller is configured to communicate the one or more sensed parameters to the remote device external to the patient via the second communications module.

Alternatively or additionally, the one or more sensors may include one or more of an accelerometer, a gyroscope, an impendence sensor, an electrogram sensor, a force sensor, an audio sensor and a button.

Alternatively or additionally, the bridge device may further include a user interface that is operably coupled to the controller. The controller may be configured to communicate with the patient via the user interface and the user interface may include one or more of a vibrator, a speaker and a Light Emitting Diode (LED).

Alternatively or additionally, the housing may have a first side and an opposing second side, and the first side may have at least two of the plurality of electrodes.

Alternatively or additionally, the second side may have at least two of the plurality of electrodes.

Alternatively or additionally, the housing may have a side wall extending between the first side and the second side and the side wall may have at least one of the plurality of electrodes.

Alternatively or additionally, the first side may have at least four electrodes arranged in a kite configuration.

In another example of the disclosure, an external bridge device may be configured to serve as a communications bridge between a medical device implantable within a patient and a remote device exterior to the patient, the external bridge device configured to communicate with the medical device implantable within a patient via conducted communication and to communicate with the remote device exterior to the patient using a wireless communications protocol. The external bridge device includes a substrate and two or more electrodes that are disposed on the substrate such that the two or more electrodes are configured to be temporarily disposed in contact with the patient's skin. A controller is operably coupled to the two or more electrodes and is configured to receive conducted communication from the medical device implantable within a patient via two of the two or more electrodes. A transceiver is operable coupled to the controller. The controller is configured to receive information via conducted communication and to transmit the information to the remote device exterior to the patient via the transceiver.

Alternatively or additionally, the external bridge device may further include one or more sensors that are operatively coupled to the controller for sensing one or more sensed parameters, wherein the controller is configured to communicate the one or more sensed parameters to the remote device via the transceiver.

The above summary of some illustrative embodiments is not intended to describe each disclosed embodiment or every implementation of the present disclosure. The Figures, and Description, which follow, more particularly exemplify some of these embodiments.

BRIEF DESCRIPTION OF THE DRAWINGS

The disclosure may be more completely understood in consideration of the following description in connection with the accompanying drawings, in which:

FIG. 9 is a schematic view of a bridge device deployed relative to a patient's chest and touching the patient's skin;

Figure 1:
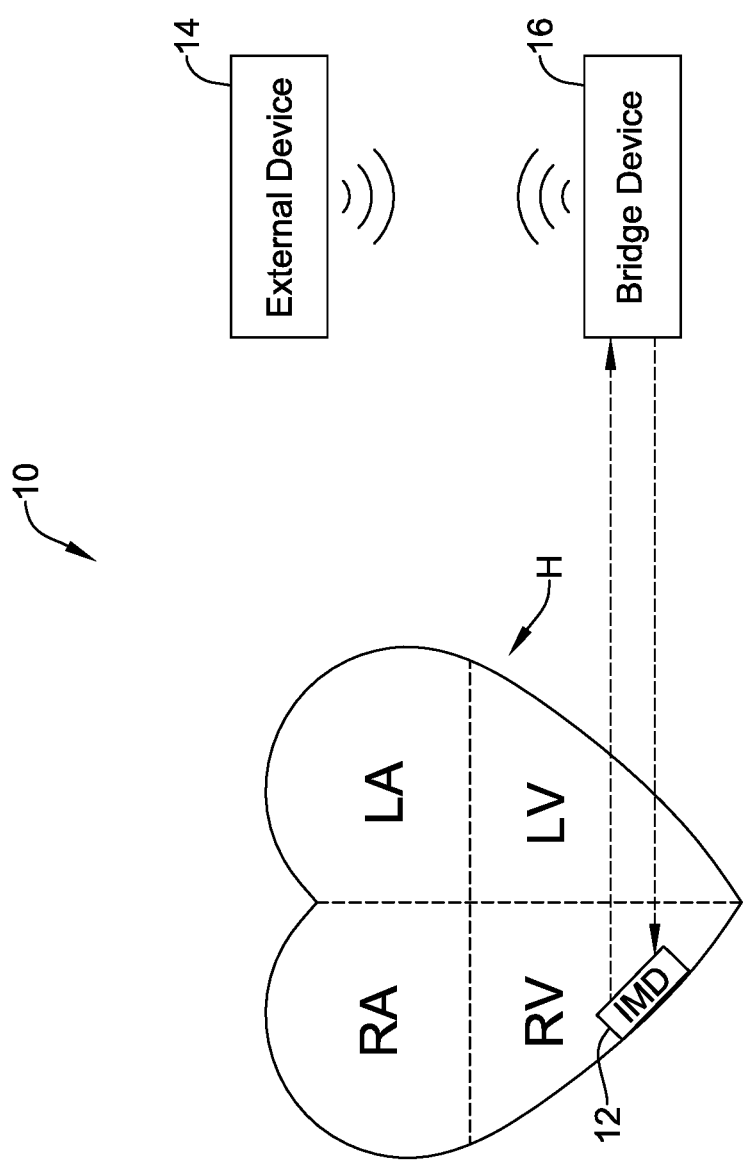
FIG. 1 is a schematic block diagram of a system including an implantable medical device (IMD), an external device and a bridge device to facilitate communication between the IMD and the external device in accordance with an example of the disclosure.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following description should be read with reference to the drawings in which similar structures in different drawings are numbered the same. The drawings, which are not necessarily to scale, depict illustrative embodiments and are not intended to limit the scope of the disclosure. While the present disclosure is applicable to any suitable implantable medical device (IMD), the description below often uses leadless cardiac pacemakers (LCP) and implantable cardioverter-defibrillator (ICD) and/or pacemakers as particular examples.

FIG. 1 is a schematic block diagram of a system that includes an implantable medical device (IMD) 12, an external device 14 and a handheld bridge device 16 to facilitate communication between the IMD 12 and the external device 14 in accordance with an example of the disclosure. In some cases, the IMD 12 may sense and/or pace a heart H. In some cases, the IMD 12 may be configured to shock the heart H. In some cases, the IMD 12 may be a diagnostic sensor that is configured to capture and provide diagnostic data, sometimes to the external device 14 via the bridge device 16.

In the example shown, the implantable medical device (IMD) 12 may be deployed near or even within the heart H. The implanted location of the IMD 12 may be considered as being an implant site. As illustrated, the IMD 12 is shown implanted in the right ventricle LV. This is merely illustrative, as the IMD 12 may be implanted within any other chamber of the heart H, or may be implanted within the patient but external to the heart H.

In some cases, there may be a desire to communicate with the IMD 12. For example, there may be a desire to transfer sensor data and other cardiac-related information that may be sensed by the IMD 12 to an external device 14. In some cases, due to its proximity to the heart H, the IMD 12 may be in a position to obtain more accurate cardiac electrical signals than can be obtained from skin electrodes or the like. In some instances, there may be a desire to upload at least some of this information so that it can be more easily viewed and/or analyzed. In some cases, there may be a desire to transmit cardiac data from the IMD 12 so that a remote physician or monitoring service can see how the patient is doing, which may allow routine periodic reviews as well as reviews during particular situations in which the patient is not feeling well. In some cases, it may be desirable to send commands and/or requests to the IMD 12 from an external device 14. In some cases, the IMD 12 may be a Leadless Cardiac Pacemaker (LCP) that is configured to communicate with other devices using conducted communication.

The external device 14 may be any device external to the patient that is configured to receive, send and/or analyze information. In some cases, the external device 14 may be configured to display cardiac data received from the IMD 12 via the handheld bridge device 16. In some instances, the external device 14 may be used to transmit parameters and other configuration data to the IMD 12 via handheld bridge device 16 in order to control or optimize operation of the IMD 12. In some cases, the external device 14 may be a programmer. In some cases, the external device 14 may be a portable device such as a tablet or smartphone that can receive cardiac data and/or other information from the IMD 12 via handheld bridge device 16, and can then display the cardiac data and/or other information and/or communicate the cardiac data and/or other information elsewhere via a cellular network, WiFi, Bluetooth and the like. In some cases, the external device 14 may be a gateway or the like (e.g. router and/or access point) that can receive the cardiac data and/or other information from the IMD 12 via the handheld bridge device 16 and transmit the data and/or other information to a remote server or the like, such as a remote server that is accessible by a physician.

In some instances, the communication protocols used by the IMD 12 and the external device 14 may be different, and may not be compatible with each other. For example, in some cases, the IMD 12 may be configured to communicate via conducted communication while the external device 14 may use a wireless communication protocol. In conducted communication, electrical signals are transmitted or carried from the transmitter to the receiver via body tissue. While this enables communication between implanted devices, receiving conducted communication from outside the body typically requires physical contact with the patient's skin in order to pick up the electrical impulses carried by the body tissue. As illustrated, the system 10 may include a bridge device 16. As will be discussed, the bridge device 16 may be handheld and may include electrical contacts that can be presses against the patient's skin, and when so provided, communicate with the IMD 12 via conducted communication. The bridge device may also be configured to communicate with the external device 14 via a wireless or wired communication protocol (e.g. RF communication, IR communication, inductive communication).

It will be appreciated that communication between the external device 14 and the bridge device 16 may be unidirectional or bidirectional, and communication between the bridge device 16 and the IMD 12 may be unidirectional or bidirectional. In some cases, the IMD 12 may be configured to periodically transmit particular data, and if the bridge device 16 is in skin contact, the bridge device 16 may receive the transmitted data. In some instances, the IMD 12 may only transmit particular data after receiving a request for the data from the bridge device 16. In some cases, the request may originate in the external device 14 and may be transmitted via conducted communication to the IMD 12 via the bridge device 16. In some cases, the bridge device 16 may include one or more sensors, such as an ECG sensor, an accelerometer, a resistance sensor, a gyroscope, and/or any other suitable sensor or sensor combination, and may provide the sensed data to the external device 14 and/or IMD 12.

Figure 2:
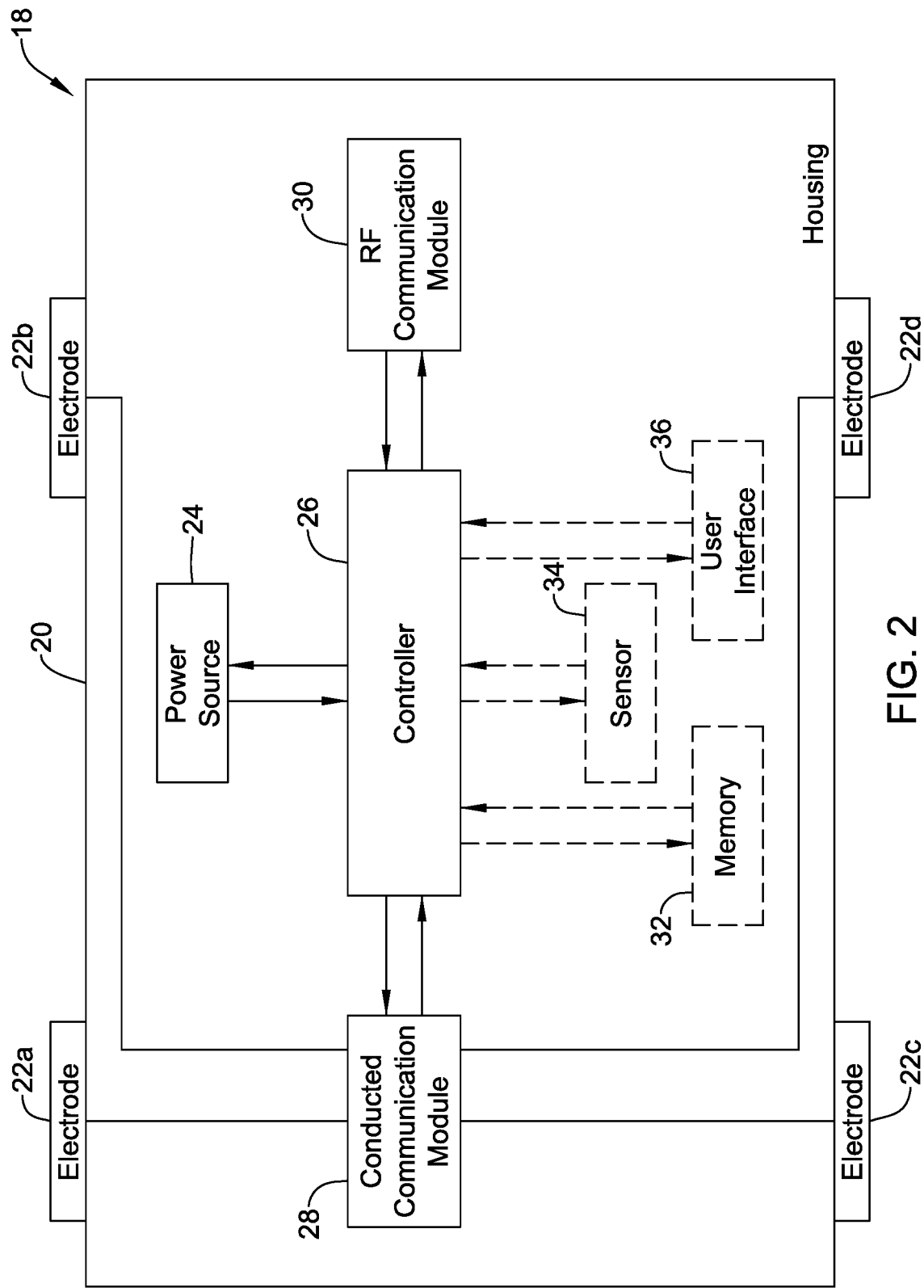
FIG. 2 is a schematic block diagram of a bridge device useable in the system of FIG. 1 in accordance with an example of the disclosure.

FIG. 2 is a schematic block diagram of an illustrative bridge device 18 that may be considered as being a manifestation of the bridge device 16 (FIG. 1). The bridge device 18 may be considered as providing a communication bridge between a leadless cardiac pacemaker (an example of the IMD 12) and a smartphone (an example of the external device 14). In some cases, the bridge device 18 may be handheld and may include a housing 20 and a plurality of electrodes 22a, 22b, 22c, 22d that are exposed outside of the housing 20. In some cases, at least two of the plurality of electrodes 22a, 22b, 22c, 22d are positioned so that they can be concurrently placed in contact with a patient's skin. While a total of four electrodes 22a, 22b, 22c, 22d are illustrated in FIG. 2, it will be appreciated that in some cases, there may be only two electrodes, or three electrodes. In some cases, there may be five or more electrodes on the housing 20.

In some cases, having multiple electrodes enables additional communication vectors for communicating with the IMD 12. In some instances, having multiple electrodes enables Kelvin sensing in which a first pair of electrodes is used to provide a current and a second pair of electrodes is used to sense a resulting voltage. The illustrative bridge device 18 also includes a power source 24 that is disposed within the housing 20. The power source 24 may be a rechargeable battery or a non-rechargeable battery, for example, or a capacitor. A controller 26 is also disposed within the housing 20 and is operably powered by the power source 24. In some cases, the controller 26 may be configured to sequentially test various communication vectors using various pairs of the electrodes 22a, 22b, 22c, 22d, and may select a particular communication vector that, for example provides the highest signal-to-noise ratio (SNR) for subsequent use.

In the example shown, a conducted communications module 28 is disposed within the housing 20 and is operably coupled to the controller 26 and to at least two of the plurality of electrodes 22a, 22b, 22c, 22d. In some cases, the conducted communications module 28 is configured to allow the controller 26 to communicate with a leadless cardiac pacemaker (such as the IMD 12 of FIG. 1) via at least two of the plurality of electrodes 22a, 22b, 22c, 22d using conducted communication. In the example shown, an RF communications module 30 is also disposed within the housing 20 and is operably coupled to the controller 26. In some cases, the RF communications module 30 is configured to allow the controller 26 to communicate with a smartphone (as an example of the external device 14) external to the patient using RF communication (e.g. WiFi, Bluetooth, etc.).

In some cases, the bridge device 18 may also include a memory 32 that is operably coupled to the controller 26 such that information received from the leadless cardiac pacemaker by conducted communication via the at least two of the plurality of electrodes 22a, 22b, 22c, 22d can be saved to the memory 32 prior to subsequent communication of the information to the smartphone via the RF communications module 30. In some cases, the bridge device 18 may also include one or more sensors 34 operatively coupled to the controller 26 for sensing one or more sensed parameters. The controller 26 may be configured to communicate the one or more sensed parameters to the smartphone via the RF communications module 30.

In some instances, the one or more sensors 34 (only one is illustrated) may include one or more of an accelerometer, a gyroscope, an impendence sensor, an electrogram sensor, a force sensor, an audio sensor, a user actuatable button or switch, and/or any other suitable sensor or sensor combination. In some cases, the one or more sensors 34 may enable the bridge device 18 to sense an electrocardiogram of the patient's heart independently of any electrocardiogram that may be sensed by the IMD 12 and communicated to the bridge device 18 via conducted communication from the IMD 12. In another example, the one or more sensors 34 may enable the bridge device 18 to sense respiration or other information. The one or more sensors 34 may collect and provide additional cardiac and/or other physiologic data beyond that sensed by and received from the IMD 12.

In some cases, the bridge device 18 may include a user interface 36 that is operably coupled to the controller 26 such that the controller 26 is able to communicate with the patient via the user interface 36. In some cases, the bridge device 18 may provide a visual or auditory reminder that it is time to place the bridge device 18 in position relative to the patient's skin (e.g. on the patient's chest) so that the bridge device 18 may communicate with the IMD 12 (FIG. 1). In some cases, the bridge device 18 may provide feedback to the user as to whether they have properly placed the bridge device 18. For example, the bridge device 18 may provide a first communication, sort of a "getting warmer" if the bridge device 18 is being moved closer to an optimal position, and a second communication, sort of a "getting colder" if the bridge device 18 is being moved away from an optimal or even satisfactory position. The optimal or even satisfactory position may be based at least part on, for example, an acceptable SNR for conducted communication with the IMD 12, and/or an acceptable SNR from the one or more sensors 34 when sensing desired physiologic parameter. These are just examples. The first and second communications may be different lights or colors, or different sounds, or even different vibrations. In some cases, the user interface 36 may provide an indication of remaining battery life. Accordingly, in some cases, the user interface 36 may include one or more of a vibrator, a speaker, a Light Emitting Diode (LED), and/or an LCD display, for example.

In some cases, the controller 40 may communicate information to the external device 14, and the external device 14 may use that information to provide instructions to the user via a user interface of the external device 14. For example, the external device 14 may provide a notification to the user via the user interface of the external device 14 that it is time to place the bridge device 38 in position relative to the patient's skin so that the bridge device 18 may communicate with the IMD 12 (FIG. 1). In some cases, the external device 14 may provide feedback to the user as to whether they have properly placed the bridge device 38 on the patient's skin. These are just examples.

In some cases, the external device 14 may be a smartphone and/or tablet computer running an application program. The application program may provide instruction to a user, provide trend analysis, allow a user to selectively control the IMD 12 and/or bridge device 18, provide reminders to a user, store historical data for later download and/or analysis, and/or perform other tasks. With respect to instructions, the application program may provide the user with instructions on how and/or when to apply the bridge device 18 to the patient's skin, and when and/or how to start a new session. The application program may aid in pairing the smartphone and/or tablet computer with the bridge device 18 (e.g. Bluetooth, Wifi). The application program may provide notifications to the user, such as when communication with the bridge device 18 has been lost, when the battery charge of the bridge device 18 is low, etc. With respect to trend analysis, the application program may keep track of trends in certain predetermined parameters. For example, the application program may keep track of and sometimes display a trend in heart rate, a trend in the percent of heart beats that are paced versus intrinsic beats, and/or a trend in other suitable parameter(s). These are just examples. With respect to selectively controlling the IMD 12 and/or bridge device 18, the application program may allow certain functions and/or parameters of the IMD 12 and/or bridge device 18 to be changed by the patient, and/or certain functions and/or parameters of the IMD 12 and/or bridge device 18 to be changed by a physician. For example, the application program may provide access control via user provided credentials. The user provided credentials may include passwords, finger print scans, retina scans, etc. In some cases, different users may have different permissions. For example, the patient may have very limited rights to perform certain functions and/or change certain parameters of the IMD 12 and/or bridge device 18. A physician may have additional rights to perform more functions and/or change more parameters of the IMD 12 and/or bridge device 18. A manufacturer of the IMD 12 and/or bridge may have even more rights to perform certain functions and/or change parameters of the IMD 12 and/or bridge device 18. With respect to reminders, the application program may notify the patient that it is time to start a new session, time to take certain medications, and/or provide other reminders to the patient as desired. These are just examples.

Figure 3:
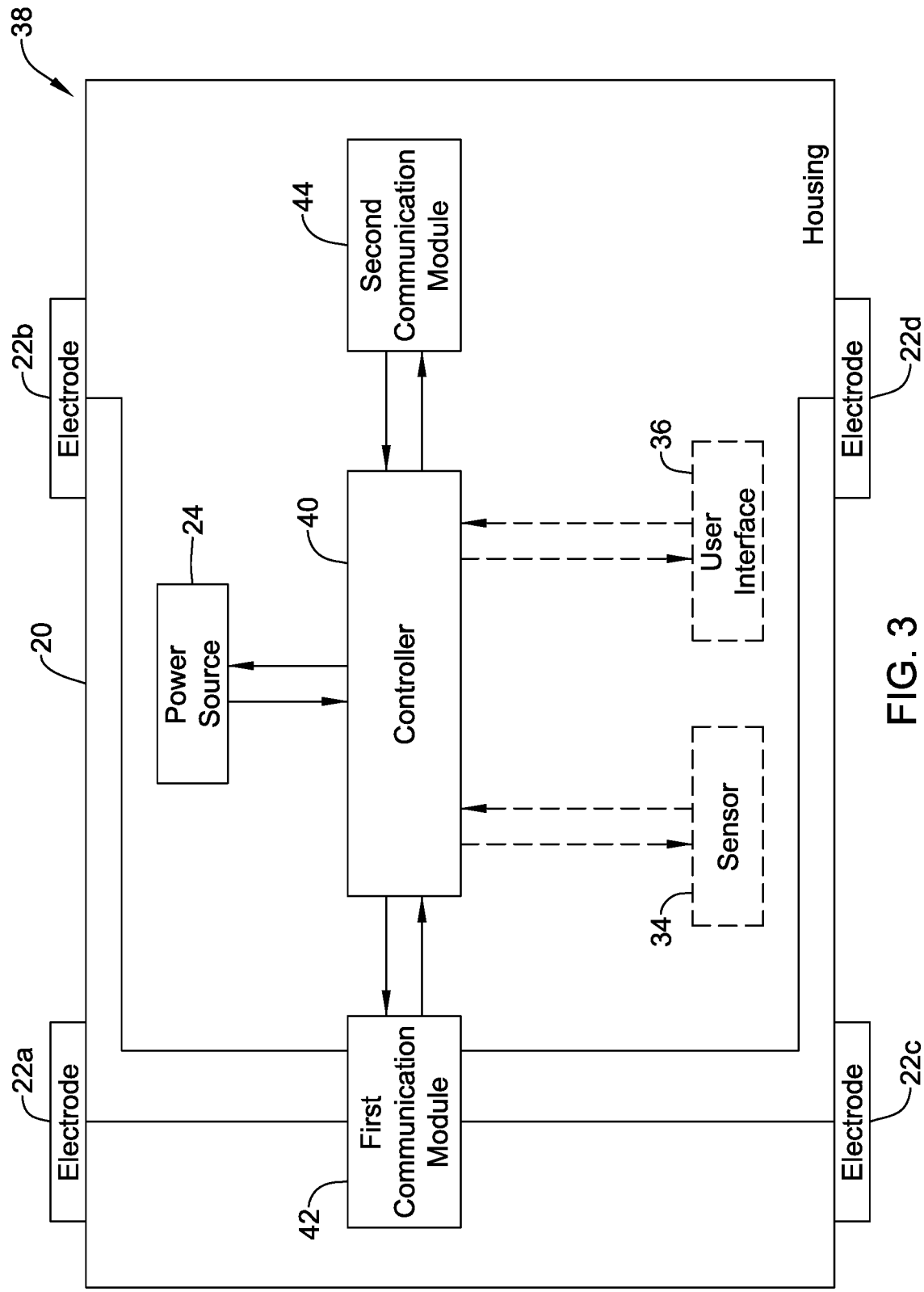
FIG. 3 is a schematic block diagram of a bridge device useable in the system of FIG. 1 in accordance with an example of the disclosure.

FIG. 3 is a schematic block diagram of a bridge device 38 that may, for example, be considered as being a manifestation of the bridge device 16 (FIG. 1). The bridge device 38 may be configured to provide a communication bridge between an implantable medical device (such as but not limited to the IMD 12) and a remote device external to the patient (such as but not limited to the external device 14). In some cases, the bridge device 38 may include a housing 20 and a plurality of electrodes 22a, 22b, 22c, 22d that are exposed outside of the housing 20. In some cases, at least two of the plurality of electrodes 22a, 22b, 22c, 22d are positioned so that they can be concurrently placed in contact with a patient's skin. While a total of four electrodes 22a, 22b, 22c, 22d are illustrated, it will be appreciated that in some cases, there may be only two electrodes, or three electrodes. In some cases, there may be five or more electrodes on the housing 20. The illustrative bridge device 38 also includes the power source 24 that is disposed within the housing 20. The power source 24 may be a rechargeable battery or a non-rechargeable battery, for example, or a capacitor. A controller 40 is disposed within the housing 20 and is operably powered at least in part by the power source 24.

The bridge device 38 includes a first communications module 42 that is disposed within the housing 20 and is operably coupled with the controller 40 as well as being coupled to at least two of the plurality of electrodes 22a, 22b, 22c, 22d. In some cases, the first communications module 42 may be configured to allow the controller 40 to communicate with an implantable medical device (such as the IMD 12) via at least two of the plurality of electrodes 22a, 22b, 22c, 22d using conducted communication.

The illustrative bridge device 38 also includes a second communications module 44 that is disposed within the housing 20 and is operably coupled to the controller 40. The second communications module 44 may be configured to allow the controller 40 to communicate with a remote device external to the patient (such as the external device 14). In some cases, the implantable medical device with which the first communications module 42 communicates may be a leadless cardiac pacemaker and the external device with which the second communications module 44 communicates with may be a smartphone or tablet computer.

In some cases, the second communications module 44 may be configured to allow the controller 40 to communicate with the remote device external to the patient using wireless communication. In some instances, the wireless communication may include Radio Frequency (RF) communication. Illustrative but non-limiting examples of wireless communication useable by the second communications module 44 include one or more of Bluetooth communication, WiFi communication, inductive communication, infrared (IR) communication and optical communication. These are just examples. In some cases, the second communications module 44 may be configured to allow the controller 40 to communicate with the remote device external to the patient using wired communication.

In some cases, as discussed relative to the bridge device 18 of FIG. 2, the bridge device 38 may include one or more sensors 34 operatively coupled to the controller 40 for sensing one or more sensed parameters. In some instances, the one or more sensors 34 (only one is illustrated) may include one or more of an accelerometer, a gyroscope, an impendence sensor, an electrogram sensor, a force sensor, an audio sensor, a user actuatable button or switch, and/or any other suitable sensor or sensor combination. In some cases, the one or more sensors 34 may provide additional cardiac and/or other physiologic data beyond that sensed by and received from the IMD 12. The data from the one or more sensors 34 may include one or more sensed parameters that may be communicated to the remote device external to the patient via the second communications module 44, and/or may be communicated to the IMD 12 via the first communications module 42.

In some cases, the bridge device 38 may include a user interface 36 that is operably coupled to the controller 40 such that the controller 40 is able to communicate with the patient via the user interface 36. In some cases, the bridge device 38 may provide a visual or auditory reminder that it is time to place the bridge device 38 in position relative to the patient's skin so that the bridge device 38 may communicate with the IMD 12 (FIG. 1). In some cases, the bridge device 38 may provide feedback to the user as to whether they have properly placed the bridge device 38 on the patient's skin. In some cases, the user interface 36 may include one or more of a vibrator, a speaker, a Light Emitting Diode (LED), and/or a display, for example.

In some cases, the controller 40 may communicate information to the external device 14, and the external device 14 may use that information to provide instructions to the user via a user interface of the external device 14. For example, the external device 14 may provide a notification to the user via the user interface of the external device 14 that it is time to place the bridge device 38 in position relative to the patient's skin so that the bridge device 18 may communicate with the IMD 12 (FIG. 1). In some cases, the external device 14 may provide feedback to the user as to whether they have properly placed the bridge device 38 on the patient's skin. These are just examples.

Figure 4:
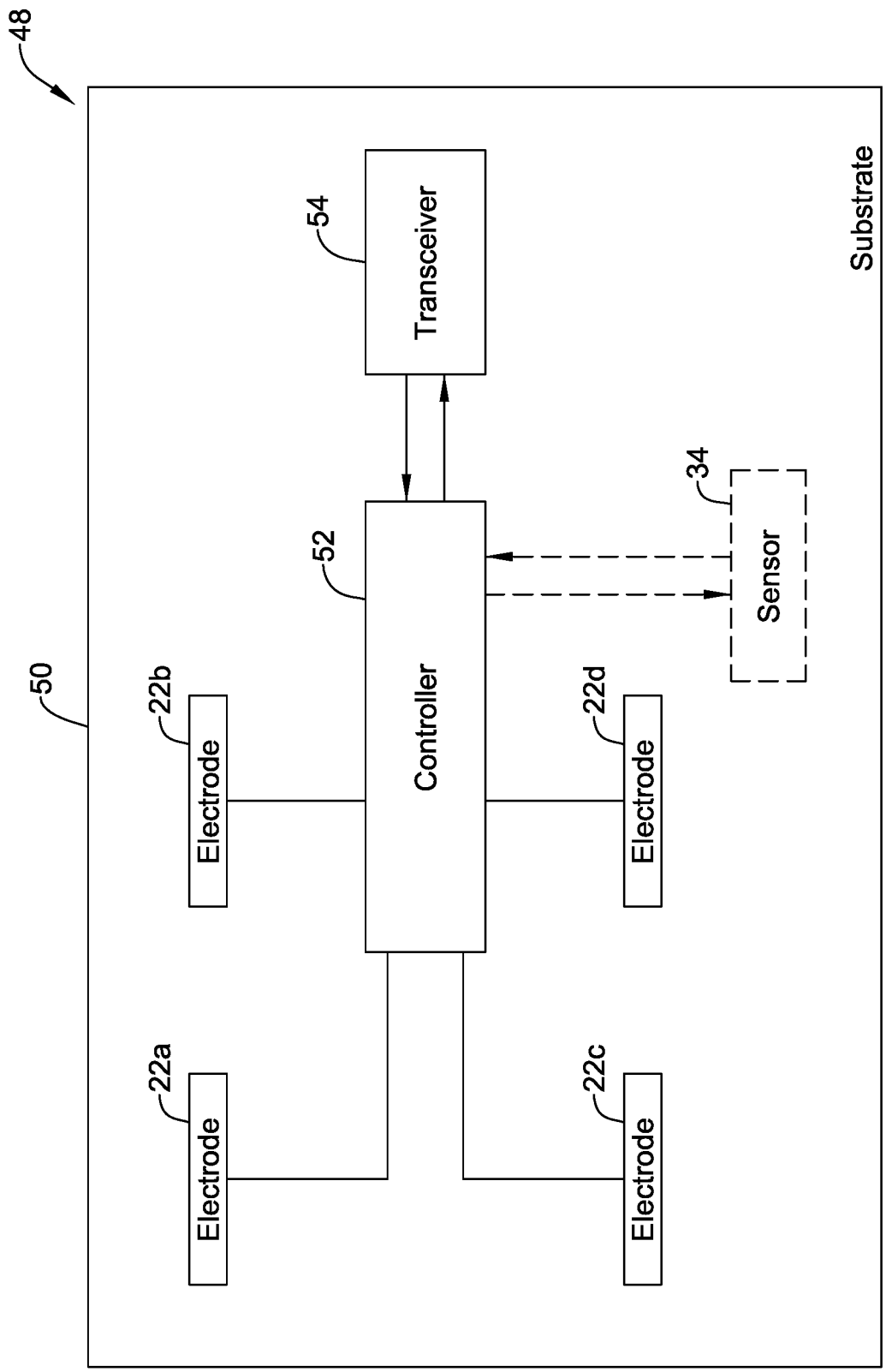
FIG. 4 is a schematic block diagram of a bridge device useable in the system of FIG. 1 in accordance with an example of the disclosure.

FIG. 4 is a schematic block diagram of an external bridge device 48 that may, for example, be considered as being a manifestation of the bridge device 16 (FIG. 1). The external bridge device 48 may be configured to provide a communication bridge between an implantable medical device (such as but not limited to the IMD 12) and a remote device external to the patient (such as but not limited to the external device 14). In some cases, the external bridge device 48 may include a substrate 50 and a plurality of electrodes 22a, 22b, 22c, 22d that are disposed on the substrate 50. In some cases, at least two of the plurality of electrodes 22a, 22b, 22c, 22d are positioned so that they can be concurrently placed in contact with a patient's skin. While a total of four electrodes 22a, 22b, 22c, 22d are illustrated, it will be appreciated that in some cases, there may be only two electrodes, or three electrodes. In some cases, there may be five or more electrodes on the substrate 50.

The illustrative external bridge device 48 includes a controller 52 that is operably coupled to the two or more electrodes 22a, 22b, 22c, 22d and that is configured to receive conducted communication from a medical device implantable within a patient via two of the two or more electrodes 22a, 22b, 22c, 22d. A transceiver 54 is operably coupled to the controller 52. In some cases, the controller 52 is configured to receive information from the implantable medical device via conducted communication and to transmit the information to the remote device exterior to the patient via the transceiver 54. In some case, the external bridge device 48 may include one or more sensors 34 that are operably coupled to the controller 52 for sensing one or more sensed parameters. In some instances, the controller 52 may be configured to communicate the one or more sensed parameters to the remote device via the transceiver 54.

FIGS. 5 through 8 provide illustrative but non-limiting examples of electrode arrangements for the bridge device 16. These electrode arrangements may, for example, be utilized with any of bridge device 18 (FIG. 2), the bridge device 38 (FIG. 3) or the external bridge device 48 (FIG. 4). It will be appreciated that features or portions of the electrode configurations shown in FIGS. 5 through 8 may be mixed and matched, as desired. In some cases, at least some features of the bridge device may be built into a smartphone case that may be secured to a smartphone. In some cases, the bridge device may be configured to be adhesively secured to the back of a smartphone case, with at least some of the electrodes exposed so the electrodes can be brought into engagement with the patient's skin.

Figure 5:
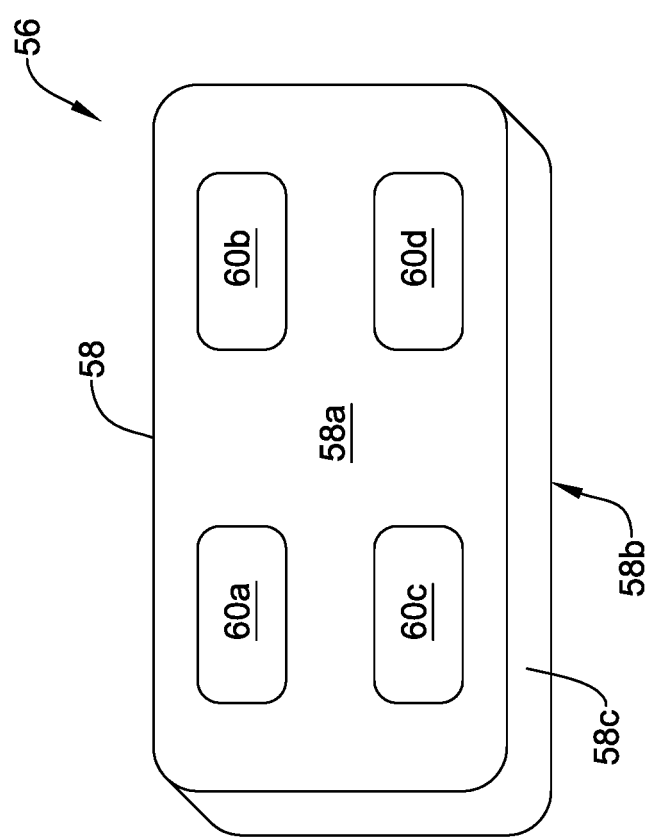
FIG. 5 is a perspective view of a bridge device useable in the system of FIG. 1 in accordance with an example of the disclosure.

FIG. 5 is a perspective view of an illustrative bridge device 56 having a housing 58. While the housing 58 is illustrated as being rectilinear, and having an overall size perhaps the size of an average smartphone and thus can be easily hand held, this is merely illustrative. In some cases, the housing 58 may be circular or ovoid, and may be of any suitable dimensions. The housing 58 defines a first surface 58a and an opposing second surface 58b, with a peripheral side wall 58c extending between the first surface 58a and the second surface 58b.

A total of four electrodes 60a, 60b, 60c, 60d are shown disposed on the first surface 58a of the housing 58. In some cases, having a plurality of electrodes 60a, 60b, 60c, 60d enable the use of various communication vectors, each using a different pair of the electrodes 60a, 60b, 60c, 60d. In some instances, as noted above, having at least four electrodes 60a, 60b, 60c, 60d enables the use of Kelvin sensing. While four electrodes 60a, 60b, 60c, 60d are shown, the bridge device 56 may include any number of electrodes 60a, 60b, 60c, 60d. In some cases, as shown, the electrodes 60a, 60b, 60c, 60d are rectilinear in shape, but this is not required, as other shapes are contemplated.

Figure 6:
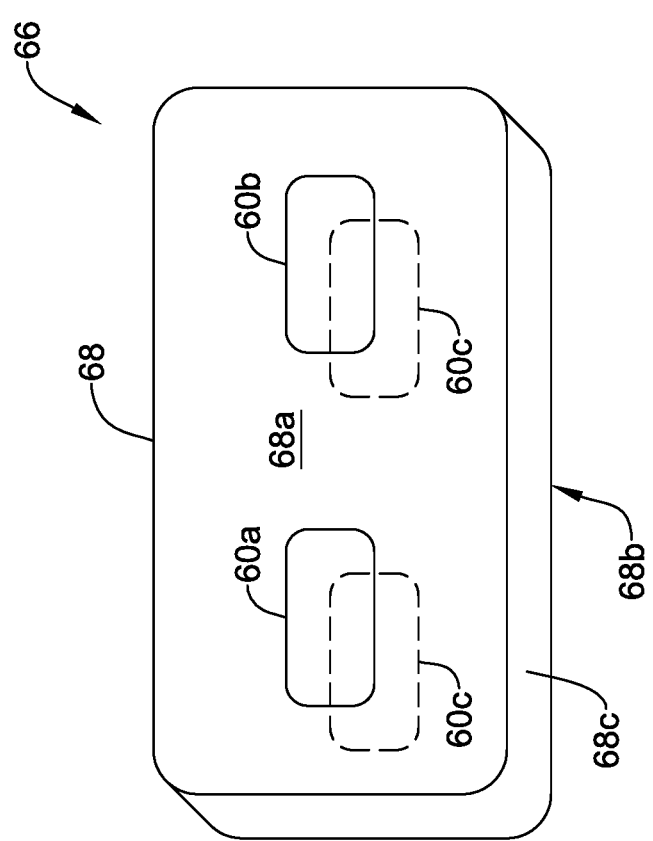
FIG. 6 is a schematic block diagram of a bridge device useable in the system of FIG. 1 in accordance with an example of the disclosure.

FIG. 6 is a perspective view of another illustrative bridge device 66 having a housing 68. While the housing 68 is illustrated as being rectilinear, and having an overall size perhaps the size of an average smartphone, this is merely illustrative. In some cases, the housing 68 may be circular or ovoid, and may be of any suitable dimensions. The housing 68 defines a substantially first surface 68a and an opposing second surface 68b, with a peripheral side wall 68c extending between the first surface 68a and the second surface 68b. The illustrative bridge device 66 includes a total of four electrodes, with two electrodes 60a, 60b disposed on the first surface 68a and two electrodes 60c, 60d (seen in phantom) disposed on the second opposing surface 68b. In some cases, having electrodes on both sides of the housing 68 may allow either side of the bridge device 56 to be placed against the patient's chest. The controller inside the bridge device 56 may be configured to automatically detect which side of the bridge device 56 is placed against the skin and operate accordingly. In some cases, the electrodes on one side (say the electrodes 60a, 60b) may be held against the patient's chest to support conducted communication with an IMD 12, and the electrodes on the other side (say the electrodes 60c, 60d) may make contact with the patient's fingers, which may provide another communication and/or sense vector.

Figure 7:
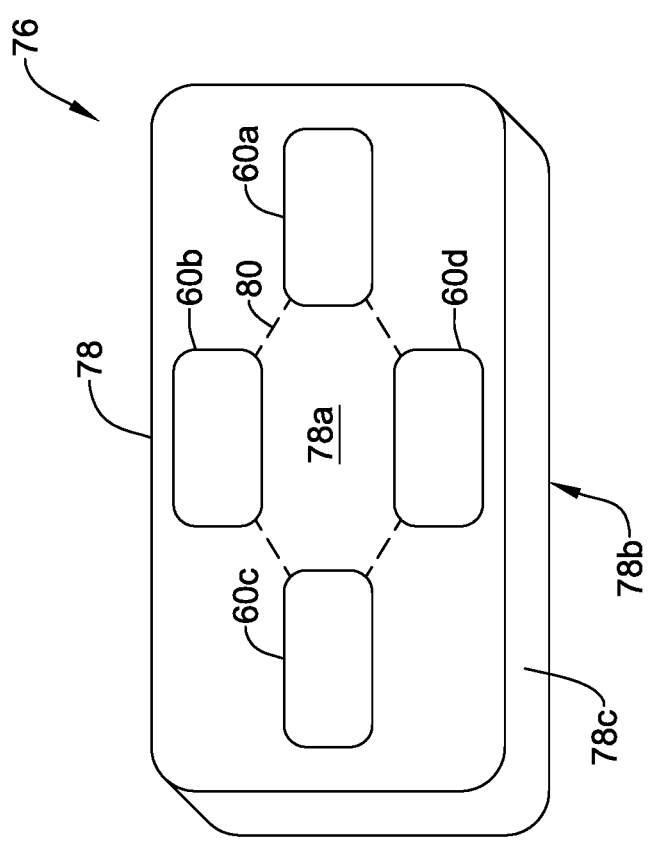
FIG. 7 is a schematic block diagram of a bridge device useable in the system of FIG. 1 in accordance with an example of the disclosure.

FIG. 7 is a perspective view of another illustrative bridge device 76 having a housing 78. While the housing 78 is illustrated as being rectilinear, and having an overall size perhaps the size of an average smartphone, this is merely illustrative. In some cases, the housing 78 may be circular or ovoid, and may be of any suitable dimensions. The housing 78 defines a first surface 78a and an opposing second surface 78b, with a peripheral side wall 78c extending between the first surface 78a and the second surface 78b. A total of four electrodes 60a, 60b, 60c, 60d are shown disposed on the first surface 78a. In some cases, having a plurality of electrodes 60a, 60b, 60c, 60d on the first surface 78a may provide a variety of communication vectors for communication with an IMD 12. In some cases, as illustrated, the electrodes 60a, 60b, 60c, 60d may be laid out in a kite-shape, as shown by dashed kite shape 80. In some instances, having the electrodes 60a, 60b, 60c, 60d in this "kite" configuration may provide a useful variety of communication vectors.

Figure 8:
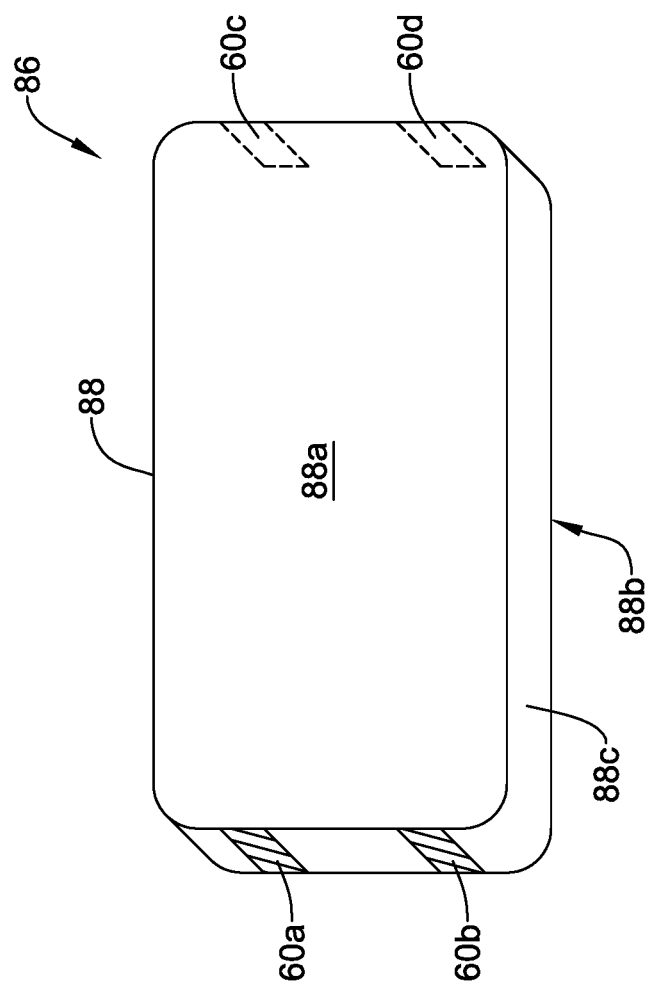
FIG. 8 is a schematic block diagram of a bridge device useable in the system of FIG. 1 in accordance with an example of the disclosure.

FIG. 8 is a perspective view of another illustrative bridge device 86 having a housing 88. While the housing 88 is illustrated as being rectilinear, and having an overall size perhaps the size of an average smartphone, this is merely illustrative. In some cases, the housing 88 may be circular or ovoid, and may be of any suitable dimensions. The housing 88 defines a first surface 88a and an opposing second surface 88b, with a peripheral side wall 88c extending between the first surface 88a and the second surface 88b. In this example, a total of four electrodes 60a, 60b, 60c, 60d are disposed on the peripheral side wall 88c. Other electrodes may be positioned on the first surface 88a and/or opposing second surface 88b, if desired. In some cases, having a plurality of electrodes 60a, 60b, 60c, 60d may provide a variety of communication and/or sense vectors. In some cases, having the electrodes 60a, 60b, 60c, 60d on the peripheral side wall 88c may facilitate contact between the electrodes 60a, 60b, 60c, 60d and the skin on the fingers/hands of the person holding the bridge device 86.

Figure 10:
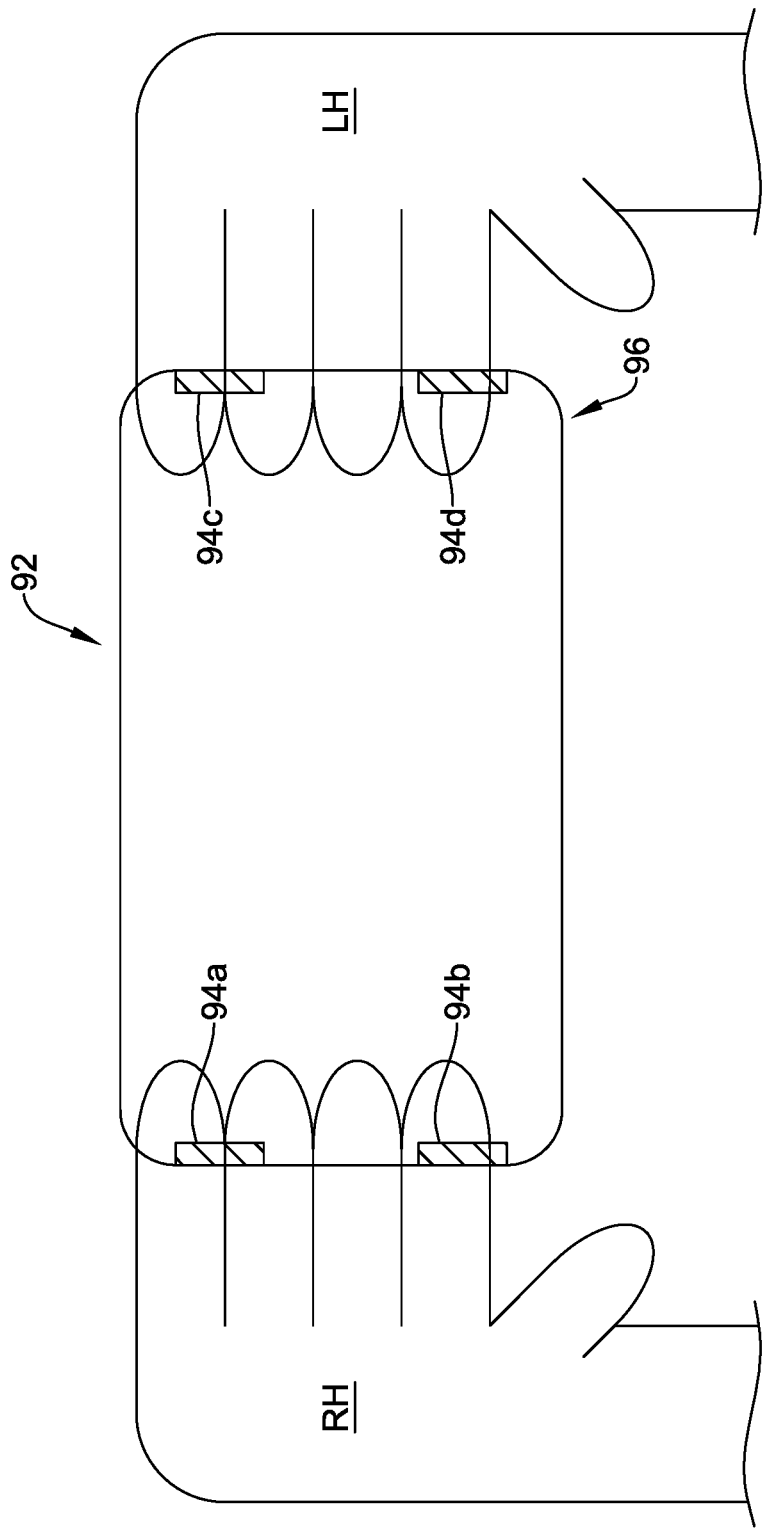
FIG. 10 is a schematic view of a bridge device deployed in a patient's hands.

FIGS. 9 and 10 provide schematic illustrations of an example of how the remote devices described herein may be deployed. FIG. 9 shows a patient P having a bridge device 90 held against the skin of the patient P. In some cases, the bridge device 90 may be positioned on the patient, near their heart H, held in place by gravity if the patient P is prone and/or held in place by the patient's hand. In some cases, the bridge device 90 may be strapped in place. In some instances, the bridge device 90 may include an adhesive layer which holds the bridge device 90 in place, with electrodes 90a, 90b, 90c, 90d in skin contact. Including an adhesive layer or a strap may enable the patient P to be sitting or standing while the bridge device 90 is in position. In some cases, rather than being held in position on the chest of the patient P, the bridge device 90 may instead be disposed within a lanyard that the patient can wear around their neck, with the bridge device 90 hanging proximate their chest. In some cases, the bridge device 90 may be built into a wrist band, intended to be worn around the patient's wrist with the electrodes 90a, 90b, 90c, 90d in skin contact.

FIG. 10 shows a patient holding a bridge device 92 in their hands. As illustrated, this shows a view from a position looking towards the front of the patient. As can be seen, the bridge device 92 may include a four electrodes 94a, 94b, 94c, 94d that are disposed along a periphery 96 of the bridge device 92. In the example shown, several fingers of the patient's right hand RH make contact with the electrodes 94a, 94b while several fingers of the patient's left hand LH make contact with the electrodes 94c, 94d. In some cases, the back side of the bridge device 92 (not visible in FIG. 10) may include additional electrodes that can be brought into engagement with the patient's skin. These additional electrodes may be provide communication electrodes and/or additional communication vectors for communication with the IMD 12. The four electrodes 94a, 94b, 94c, 94d that are disposed along the periphery 96 may provide communication vectors for communication with the IMD 12 and/or sense electrodes/vectors for sensing one or more physiologic parameters of the patient (e.g. surface EKG).

Figure 11:
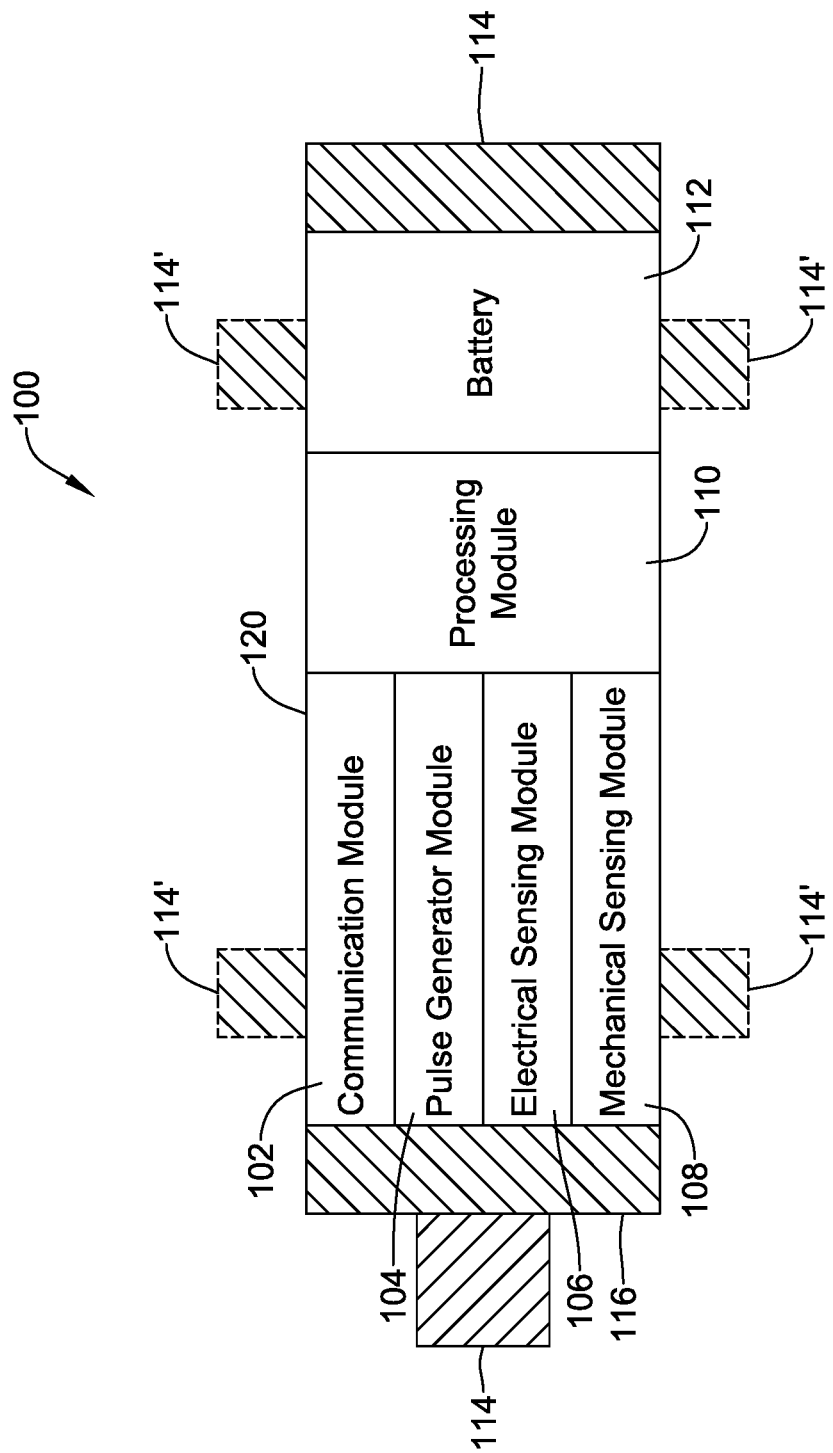
FIG. 11 is a schematic block diagram of an illustrative IMD in accordance with an example of the disclosure.

FIG. 11 depicts an illustrative leadless cardiac pacemaker (LCP) that may be implanted into a patient and may operate to deliver appropriate therapy to the heart, such as to deliver anti-tachycardia pacing (ATP) therapy, cardiac resynchronization therapy (CRT), bradycardia therapy, and/or the like. As can be seen in FIG. 11, the LCP 100 may be a compact device with all components housed within the or directly on a housing 120. In some cases, the LCP 100 may be considered as being an example of the IMD 12 (FIG. 1). In the example shown in FIG. 11, the LCP 100 may include a communication module 102, a pulse generator module 104, an electrical sensing module 106, a mechanical sensing module 108, a processing module 110, a battery 112, and an electrode arrangement 114. The LCP 100 may also include a receive coil for receiving inductive power, and a recharge circuit for recharging the battery 112 (or capacitor) using the received inductive power. It is contemplated that the LCP 100 may include more or fewer modules, depending on the application.

The communication module 102 may be configured to communicate with devices such as sensors, other medical devices such as an SICD, another LCP, and/or the like, that are located externally to the LCP 100. Such devices may be located either external or internal to the patient's body. Irrespective of the location, external devices (i.e. external to the LCP 100 but not necessarily external to the patient's body) can communicate with the LCP 100 via communication module 102 to accomplish one or more desired functions. For example, the LCP 100 may communicate information, such as sensed electrical signals, data, instructions, messages, R-wave detection markers, etc., to an external medical device (e.g. SICD, programmer and/or bridge device 16) through the communication module 102. The external medical device may use the communicated signals, data, instructions, messages, R-wave detection markers, etc., to perform various functions, such as determining occurrences of arrhythmias, delivering electrical stimulation therapy, storing received data, and/or performing any other suitable function. The LCP 100 may additionally receive information such as signals, data, instructions and/or messages from the external medical device and/or the bridge device 16 through the communication module 102, and the LCP 100 may use the received signals, data, instructions and/or messages to perform various functions, such as determining occurrences of arrhythmias, delivering electrical stimulation therapy, storing received data, and/or performing any other suitable function. The communication module 102 may be configured to use one or more methods for communicating with external devices. For example, the communication module 102 may communicate via radiofrequency (RF) signals, inductive coupling, optical signals, acoustic signals, conducted communication signals, and/or any other signals suitable for communication.

In the example shown in FIG. 11, the pulse generator module 104 may be electrically connected to the electrode arrangement 114. In some examples, the LCP 100 may additionally include electrodes 114'. In such examples, the pulse generator 104 may also be electrically connected to the electrodes 114'. The pulse generator module 104 may be configured to generate electrical stimulation signals. For example, the pulse generator module 104 may generate and deliver electrical stimulation signals by using energy stored in the battery 112 within the LCP 100 and deliver the generated electrical stimulation signals via the electrodes 114 and/or 114'. Alternatively, or additionally, the pulse generator 104 may include one or more capacitors, and the pulse generator 104 may charge the one or more capacitors by drawing energy from the battery 112. The pulse generator 104 may then use the energy of the one or more capacitors to deliver the generated electrical stimulation signals via the electrodes 114 and/or 114'. In at least some examples, the pulse generator 104 of the LCP 100 may include switching circuitry to selectively connect one or more of the electrodes 114 and/or 114' to the pulse generator 104 in order to select which of the electrodes 114/114' (and/or other electrodes) the pulse generator 104 delivers the electrical stimulation therapy. The pulse generator module 104 may generate and deliver electrical stimulation signals with particular features or in particular sequences in order to provide one or multiple of a number of different stimulation therapies. For example, the pulse generator module 104 may be configured to generate electrical stimulation signals to provide electrical stimulation therapy to combat bradycardia, tachycardia, cardiac synchronization, bradycardia arrhythmias, tachycardia arrhythmias, fibrillation arrhythmias, cardiac synchronization arrhythmias and/or to produce any other suitable electrical stimulation therapy. Some more common electrical stimulation therapies include anti-tachycardia pacing (ATP) therapy, cardiac resynchronization therapy (CRT), and cardioversion/defibrillation therapy. In some cases, the pulse generator 104 may provide a controllable pulse energy. In some cases, the pulse generator 104 may allow the controller to control the pulse voltage, pulse width, pulse shape or morphology, and/or any other suitable pulse characteristic.

In some examples, the LCP 100 may include an electrical sensing module 106, and in some cases, a mechanical sensing module 108. The electrical sensing module 106 may be configured to sense the cardiac electrical activity of the heart. For example, the electrical sensing module 106 may be connected to the electrodes 114/114', and the electrical sensing module 106 may be configured to receive cardiac electrical signals conducted through the electrodes 114/114'. The cardiac electrical signals may represent local information from the chamber in which the LCP 100 is implanted. For instance, if the LCP 100 is implanted within a ventricle of the heart (e.g. RV, LV), cardiac electrical signals sensed by the LCP 100 through the electrodes 114/114' may represent ventricular cardiac electrical signals. In some cases, the LCP 100 may be configured to detect cardiac electrical signals from other chambers (e.g. far field), such as the P-wave from the atrium.

The mechanical sensing module 108 may include one or more sensors, such as an accelerometer, a pressure sensor, a heart sound sensor, a blood-oxygen sensor, a chemical sensor, a temperature sensor, a flow sensor and/or any other suitable sensors that are configured to measure one or more mechanical/chemical parameters of the patient. Both the electrical sensing module 106 and the mechanical sensing module 108 may be connected to a processing module 110, which may provide signals representative of the sensed mechanical parameters. Although described with respect to FIG. 11 as separate sensing modules, in some cases, the electrical sensing module 106 and the mechanical sensing module 108 may be combined into a single sensing module, as desired.

The electrodes 114/114' can be secured relative to the housing 120 but exposed to the tissue and/or blood surrounding the LCP 100. In some cases, the electrodes 114 may be generally disposed on either end of the LCP 100 and may be in electrical communication with one or more of the modules 102, 104, 106, 108, and 110. The electrodes 114/114' may be supported by the housing 120, although in some examples, the electrodes 114/114' may be connected to the housing 120 through short connecting wires such that the electrodes 114/114' are not directly secured relative to the housing 120. In examples where the LCP 100 includes one or more electrodes 114', the electrodes 114' may in some cases be disposed on the sides of the LCP 100, which may increase the number of electrodes by which the LCP 100 may sense cardiac electrical activity, deliver electrical stimulation and/or communicate with an external medical device. The electrodes 114/114' can be made up of one or more biocompatible conductive materials such as various metals or alloys that are known to be safe for implantation within a human body. In some instances, the electrodes 114/114' connected to the LCP 100 may have an insulative portion that electrically isolates the electrodes 114/114' from adjacent electrodes, the housing 120, and/or other parts of the LCP 100. In some cases, one or more of the electrodes 114/114' may be provided on a tail (not shown) that extends away from the housing 120.

The processing module 110 can be configured to control the operation of the LCP 100. For example, the processing module 110 may be configured to receive electrical signals from the electrical sensing module 106 and/or the mechanical sensing module 108. Based on the received signals, the processing module 110 may determine, for example, abnormalities in the operation of the heart H. Based on any determined abnormalities, the processing module 110 may control the pulse generator module 104 to generate and deliver electrical stimulation in accordance with one or more therapies to treat the determined abnormalities. The processing module 110 may further receive information from the communication module 102. In some examples, the processing module 110 may use such received information to help determine whether an abnormality is occurring, determine a type of abnormality, and/or to take particular action in response to the information. The processing module 110 may additionally control the communication module 102 to send/receive information to/from other devices.

In some examples, the processing module 110 may include a pre-programmed chip, such as a very-large-scale integration (VLSI) chip and/or an application specific integrated circuit (ASIC). In such embodiments, the chip may be pre-programmed with control logic in order to control the operation of the LCP 100. By using a pre-programmed chip, the processing module 110 may use less power than other programmable circuits (e.g. general purpose programmable microprocessors) while still being able to maintain basic functionality, thereby potentially increasing the battery life of the LCP 100. In other examples, the processing module 110 may include a programmable microprocessor. Such a programmable microprocessor may allow a user to modify the control logic of the LCP 100 even after implantation, thereby allowing for greater flexibility of the LCP 100 than when using a pre-programmed ASIC. In some examples, the processing module 110 may further include a memory, and the processing module 110 may store information on and read information from the memory. In other examples, the LCP 100 may include a separate memory (not shown) that is in communication with the processing module 110, such that the processing module 110 may read and write information to and from the separate memory.

The battery 112 may provide power to the LCP 100 for its operations. In some examples, the battery 112 may be a non-rechargeable lithium-based battery. In other examples, a non-rechargeable battery may be made from other suitable materials, as desired. Because the LCP 100 is an implantable device, access to the LCP 100 may be limited after implantation. Accordingly, it is desirable to have sufficient battery capacity to deliver therapy over a period of treatment such as days, weeks, months, years or even decades. In some instances, the battery 112 may a rechargeable battery, which may help increase the useable lifespan of the LCP 100. A recharge circuit may receive power from a receiving coil of the LCP 100, and use the received power to recharge the rechargeable battery. In still other examples, the battery 112 may be some other type of power source, as desired.

To implant the LCP 100 inside a patient's body, an operator (e.g., a physician, clinician, etc.), may fix the LCP 100 to the cardiac tissue of the patient's heart. To facilitate fixation, the LCP 100 may include one or more anchors 116. The anchor 116 may include any one of a number of fixation or anchoring mechanisms. For example, the anchor 116 may include one or more pins, staples, threads, screws, helix, tines, and/or the like. In some examples, although not shown, the anchor 116 may include threads on its external surface that may run along at least a partial length of the anchor 116. The threads may provide friction between the cardiac tissue and the anchor to help fix the anchor 116 within the cardiac tissue. In other examples, the anchor 116 may include other structures such as barbs, spikes, or the like to facilitate engagement with the surrounding cardiac tissue.

Figure 12:
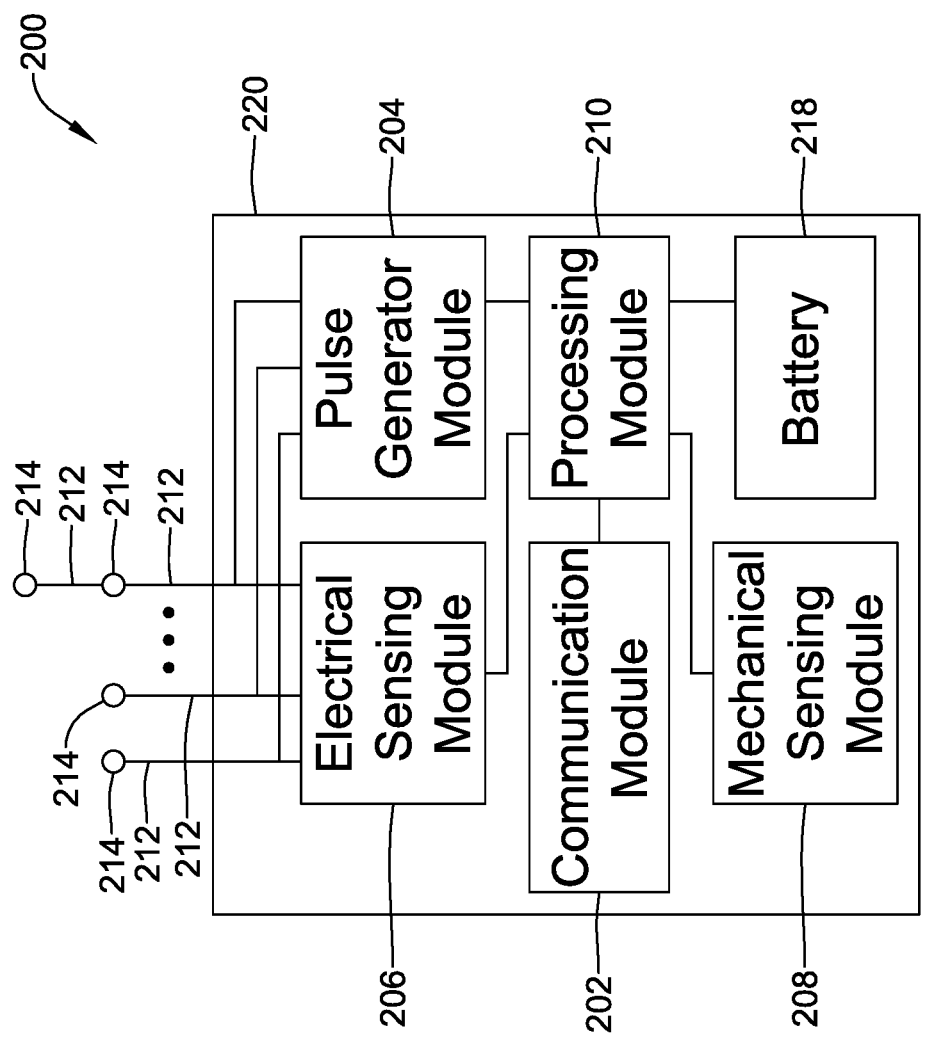
FIG. 12 is a schematic block diagram of another illustrative medical device in accordance with an example of the disclosure.

FIG. 12 depicts an example of another medical device (MD) 200, which may be used alone or in conjunction with the LCP 100 (FIG. 11), and may be used to detect and/or treat cardiac abnormalities. In some cases, the MD 200 may represent an implantable cardioverter defibrillator (ICD), a subcutaneous implantable cardioverter defibrillator (SICD) or a Leadless Cardiac Pacemaker (LCP) 100. In the example shown, the MD 200 may include a communication module 202, a pulse generator module 204, an electrical sensing module 206, a mechanical sensing module 208, a processing module 210, and a battery 218. Each of these modules may be similar to the modules 102, 104, 106, 108, and 110 of LCP 100. Additionally, the battery 218 may be similar to the battery 112 of the LCP 100. In some examples, however, the MD 200 may have a larger volume within the housing 220. In such examples, the MD 200 may include a larger battery and/or a larger processing module 210 capable of handling more complex operations than the processing module 110 of the LCP 100.

While it is contemplated that the MD 200 may be another leadless device such as shown in FIG. 11, in some instances the MD 200 may include leads such as leads 212. The leads 212 may include electrical wires that conduct electrical signals between the electrodes 214 and one or more modules located within the housing 220. In some cases, the leads 212 may be connected to and extend away from the housing 220 of the MD 200. In some examples, the leads 212 are implanted on, within, or adjacent to a heart of a patient. The leads 212 may contain one or more electrodes 214 positioned at various locations on the leads 212, and in some cases at various distances from the housing 220. Some leads 212 may only include a single electrode 214, while other leads 212 may include multiple electrodes 214. Generally, the electrodes 214 are positioned on the leads 212 such that when the leads 212 are implanted within the patient, one or more of the electrodes 214 are positioned to perform a desired function. In some cases, the one or more of the electrodes 214 may be in contact with the patient's cardiac tissue. In some cases, the one or more of the electrodes 214 may be positioned subcutaneously and outside of the patient's heart. In some cases, the electrodes 214 may conduct intrinsically generated electrical signals to the leads 212, e.g. signals representative of intrinsic cardiac electrical activity. The leads 212 may, in turn, conduct the received electrical signals to one or more of the modules 202, 204, 206, and 208 of the MD 200. In some cases, the MD 200 may generate electrical stimulation signals, and the leads 212 may conduct the generated electrical stimulation signals to the electrodes 214. The electrodes 214 may then conduct the electrical signals and delivery the signals to the patient's heart (either directly or indirectly). In some cases, a transmit coil may be supported by the lead, such at a location along the length of the lead that is near the receive coil of a remote implantable medical device.

The mechanical sensing module 208, as with the mechanical sensing module 108, may contain or be electrically connected to one or more sensors, such as accelerometers, acoustic sensors, blood pressure sensors, heart sound sensors, blood-oxygen sensors, and/or other sensors which are configured to measure one or more mechanical/chemical parameters of the heart and/or patient. In some examples, one or more of the sensors may be located on the leads 212, but this is not required. In some examples, one or more of the sensors may be located in the housing 220.

While not required, in some examples, the MD 200 may be an implantable medical device. In such examples, the housing 220 of the MD 200 may be implanted in, for example, a transthoracic region of the patient. The housing 220 may generally include any of a number of known materials that are safe for implantation in a human body and may, when implanted, hermetically seal the various components of the MD 200 from fluids and tissues of the patient's body.

In some cases, the MD 200 may be an implantable cardiac pacemaker (ICP). In this example, the MD 200 may have one or more leads, for example the leads 212, which are implanted on or within the patient's heart. The one or more leads 212 may include one or more electrodes 214 that are in contact with cardiac tissue and/or blood of the patient's heart. The MD 200 may be configured to sense intrinsically generated cardiac electrical signals and determine, for example, one or more cardiac arrhythmias based on analysis of the sensed signals. The MD 200 may be configured to deliver CRT, ATP therapy, bradycardia therapy, and/or other therapy types via the leads 212 implanted within the heart. In some examples, the MD 200 may additionally be configured provide defibrillation therapy.

In some instances, the MD 200 may be an implantable cardioverter-defibrillator (ICD) with the ability to pace. In such examples, the MD 200 may include one or more leads implanted within a patient's heart. The MD 200 may also be configured to sense cardiac electrical signals, determine occurrences of tachyarrhythmias based on the sensed signals, and may be configured to deliver defibrillation therapy in response to determining an occurrence of a tachyarrhythmia. In other examples, the MD 200 may be a subcutaneous implantable cardioverter-defibrillator (S-ICD) with the ability to pace. In examples where the MD 200 is an S-ICD, one of the leads 212 may be a subcutaneously implanted lead. In some instances, the lead(s) may have one or more electrodes that are placed subcutaneously and outside of the chest cavity. In other examples, the lead(s) may have one or more electrodes that are placed inside of the chest cavity, such as just interior of the sternum but outside of the heart H.

In some cases, the MD 200 may not include the pulse generator module 204, and may simply be an implantable diagnostic sensor medical device that is configured to capture and provide diagnostic data, sometimes to the external device 14 via the bridge device 16.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments.

What is claimed is:

1. A bridge device for providing a communication bridge between an implantable medical device configured to sense cardiac electrical activity of a patient's heart and a remote device external to the patient, the bridge device comprising:
    a housing;
    a plurality of electrodes secured to the housing and exposed outside of the housing such that at least two of the plurality of electrodes can be concurrently placed in contact with a patient's skin;
    the housing has a first side and an opposing second side, wherein the first side has at least two of the plurality of electrodes and the second side has at least one of the plurality of electrodes;
    a power source disposed within the housing;
    a controller disposed within the housing and operably powered at least in part by the power source;
    first communications electronics disposed within the housing and operably coupled to the controller and to the at least two of the plurality of electrodes that can be concurrently placed in contact with the patient's skin, the first communications electronics configured to allow the controller to communicate with an implantable medical device via at least two of the plurality of electrodes that can be concurrently placed in contact with the patient's skin using conducted communication; and
    second communications electronics disposed within the housing and operably coupled to the controller, the second communications electronics configured to allow the controller to communicate with a remote device external to the patient.

2. The bridge device of claim 1, wherein the implantable medical device is a leadless cardiac pacemaker and the remote device is a smartphone.

3. The bridge device of claim 1, wherein the second communications electronics is configured to allow the controller to communicate with the remote device external to the patient using wireless communication.

4. The bridge device of claim 3, wherein the wireless communication comprises Radio Frequency (RF) communication.

5. The bridge device of claim 3, wherein the wireless communication comprises one or more of bluetooth communication, WiFi communication, inductive communication, infrared (IR) communication and optical communication.

6. The bridge device of claim 1, wherein the second communications electronics is configured to allow the controller to communicate with the remote device external to the patient using wired communication.

7. The bridge device of claim 1, further comprising one or more sensors operatively coupled to the controller for sensing one or more sensed parameters, wherein the controller is configured to communicate the one or more sensed parameters to the remote device external to the patient via the second communications electronics.

8. The bridge device of claim 7, wherein the one or more sensors comprise one or more of an accelerometer, a gyroscope, an impendence sensor, an electrogram sensor, a force sensor, and an audio sensor.

9. The bridge device of claim 7, wherein the one or more sensors comprise one or more of an accelerometer, a gyroscope and an impendence sensor.

10. The bridge device of claim 1, further comprising a user interface operably coupled to the controller, wherein the controller is configured to communicate with the patient via the user interface, wherein the user interface comprises one or more of a vibrator, a speaker and a Light Emitting Diode (LED).

11. A system for providing a communication bridge between a leadless cardiac pacemaker and a smartphone, the system comprising:
  a leadless cardiac pacemaker;
  a smartphone;
  a bridge device comprising:
    a housing;
    a plurality of electrodes secured to the housing and exposed outside of the housing such that at least two of the plurality of electrodes can be concurrently placed in contact with a patient's skin;
    a power source disposed within the housing;
    a controller disposed within the housing and operably powered by the power source;
    conducted communications electronics disposed within the housing and operably coupled to the controller and to the at least two of the plurality of electrodes that can be concurrently placed in contact with the patient's skin, the conducted communications electronics configured to allow the controller to communicate with the leadless cardiac pacemaker via at least two of the plurality of electrodes that can be concurrently placed in contact with the patient's skin using conducted communication; and
    RF communications electronics disposed within the housing and operably coupled to the controller, the RF communications electronics configured to allow the controller to communicate with the smartphone external to the patient using RF communication;
  a memory operably coupled to the controller such that information received from the leadless cardiac pacemaker by conducted communication via the at least two of the plurality of electrodes is saved to the memory prior to subsequent communication of the information to the smartphone via the RF communications electronics;
  one or more sensors operatively coupled to the controller for sensing one or more sensed parameters, wherein the controller is configured to communicate the one or more sensed parameters to the smartphone via the RF communications electronics, wherein the one or more sensors comprise one or more of an accelerometer, a gyroscope, an impendence sensor, an electrogram sensor, and a force sensor; and
  wherein the housing has a first side and an opposing second side, wherein the first side has at least two of the plurality of electrodes and the second side has at least one of the plurality of electrodes.

12. The system of claim 11, further comprising a user interface operably coupled to the controller, wherein the controller is configured to communicate with the patient via the user interface, wherein the user interface comprises one or more of a vibrator, a speaker and a Light Emitting Diode (LED).

13. The system of claim 11, wherein the bridge device is free from a therapy delivery circuit.

14. The system of claim 11, wherein the one or more sensors comprise an impendence sensor.

* * * * *